US012709661B2

(12) United States Patent
Mizrahi et al.

(10) Patent No.: US 12,709,661 B2
(45) Date of Patent: Aug. 18, 2026

(54) POLY (MELAMINE-CO-OXALYL), METHODS OF SYNTHESIZING AND USING SAME AND ARTICLES TREATED WITH SAME

(71) Applicant: STATE OF ISRAEL, PRIME MINISTER'S OFFICE, ISRAEL INSTITUTE FOR BIOLOGICAL RESEARCH, Nes-Ziona (IL)

(72) Inventors: Dana Mizrahi, Rishon Lezion (IL); Shay Weiss, Ness Ziona (IL)

(73) Assignee: STATE OF ISRAEL, PRIME MINISTER'S OFFICE, ISRAEL INSTITUTE FOR BIOLOGICAL RESEARCH, Nes-Ziona (IL)

(*) Notice: Subject to any disclaimer, the term of this patent is extended or adjusted under 35 U.S.C. 154(b) by 677 days.

(21) Appl. No.: 18/021,431

(22) PCT Filed: Aug. 10, 2021

(86) PCT No.: PCT/IL2021/050974

§ 371 (c)(1),
(2) Date: Feb. 15, 2023

(87) PCT Pub. No.: WO2022/038593

PCT Pub. Date: Feb. 24, 2022

(65) Prior Publication Data

US 2023/0365755 A1 Nov. 16, 2023

(30) Foreign Application Priority Data

Aug. 19, 2020 (IL) .......................................... 276822

(51) Int. Cl.

*C08G 73/06* (2006.01)
*C07D 251/70* (2006.01)
*C09D 5/14* (2006.01)

(52) U.S. Cl.

CPC ......... *C08G 73/065* (2013.01); *C07D 251/70* (2013.01); *C08G 73/0644* (2013.01); *C09D 5/14* (2013.01)

(58) Field of Classification Search

CPC .......... C08F 16/28; C08F 20/60; C08G 14/10; C08G 12/32; C08G 73/065

See application file for complete search history.

(56) References Cited

U.S. PATENT DOCUMENTS

| | | | |
|---|---|---|---|
| 3,925,055 A | 12/1975 | MacDonald | |
| 5,051,459 A | 9/1991 | Slongo et al. | |
| 5,290,894 A | 3/1994 | Melrose et al. | |
| 7,845,351 B2 | 12/2010 | Mathis et al. | |
| 10,072,106 B2 | 9/2018 | Mizrahi et al. | |
| 2006/0228323 A1 | 10/2006 | Novelle et al. | |
| 2011/0076387 A1 | 3/2011 | Koehl et al. | |
| 2016/0106098 A1 | 4/2016 | Worley et al. | |
| 2018/0105618 A1* | 4/2018 | Mizrahi | A01N 43/68 |

FOREIGN PATENT DOCUMENTS

| | | |
|---|---|---|
| CN | 111019096 A | 4/2020 |
| IL | 234250 | 2/2016 |
| KR | 10-2007-0023256 A | 2/2007 |
| WO | 2006/051048 A1 | 5/2006 |

OTHER PUBLICATIONS

Huang et al (CN111019096, English translation published on Apr. 17, 2020.*

Poprac, P., et al., "Polyradical PROXYL/TEMPO-Derived Amides: Synthesis, Physicochemical Studies, DFT Calculations, and Antimicrobial Activity." ChemPlusChem, 2017, 82(11): 1326-1340.

Goldsberry, Clare "Antiviral and Antimicrobial Additive Developed for Face Masks, Medical Apparel." mddionline.com. Retrieved Feb. 16, 2023, URL: https://www.mddionline.com/design-news/antiviral-and-antimicrobial-additive-developed-face-masks-medical-apparel.

"Biomask Antiviral Face Masks with Earloop, Blue, Latex-free *Non-Returnable and Non-Cancelable*." BoundTree, Medline Industries, Inc. Item#:1031-21102, Retrieved Feb. 16, 2023.

"Curad BioMask Antiviral Isolation Mask." medline.com. Jul. 13, 2020, URL: https://www.medline.com/product/CURAD-BioMask-Antiviral-Isolation-Mask/Z05-PF07326.

Wang, L., et al., "Postfunctionalization of Porous Organic Polymers Based on Friedel-Crafts Acylation for CO2 and Hg2+ Capture." ACS Applied Materials & Interfaces, 2020, 12(32): 36652-36659.

* cited by examiner

*Primary Examiner* — Gregory Listvoyb

(74) *Attorney, Agent, or Firm* — The Roy Gross Law Firm, LLC; Roy D. Gross

(57) ABSTRACT

A polymer including a plurality of melamine monomers and at least one oxalyl linker between each pair of the monomers is disclosed. Related synthesis methods, methods of use and articles of manufacture are also disclosed.

9 Claims, 15 Drawing Sheets

102

(3)

(6)

(7)

104

(3)

(2)

(4)

(5)

Fig. 2A
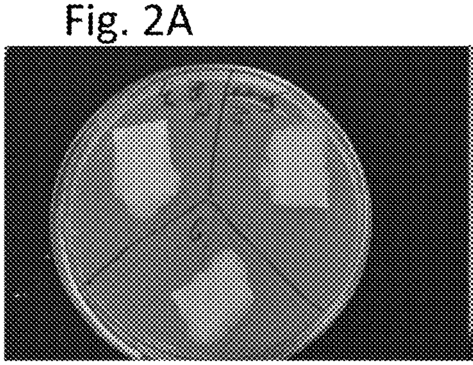
Fig. 2C
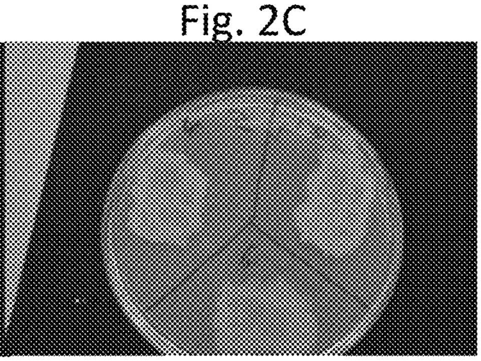
Fig. 2B
Fig. 2D

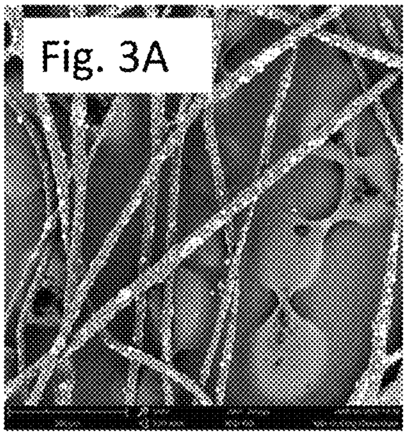
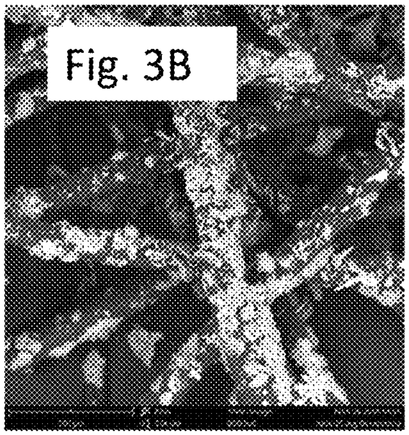
25 mg Oxalyl/acetone
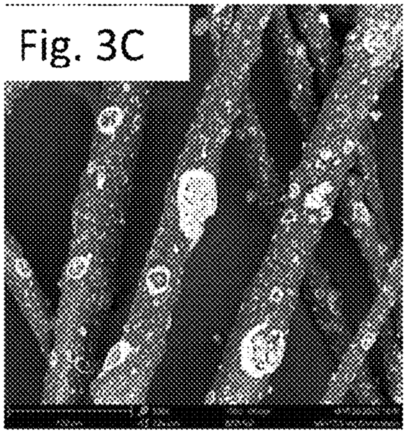
12.5 mg Oxalyl/acetone
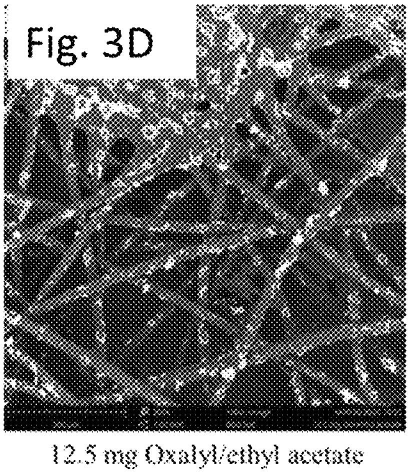
12.5 mg Oxalyl/ethyl acetate
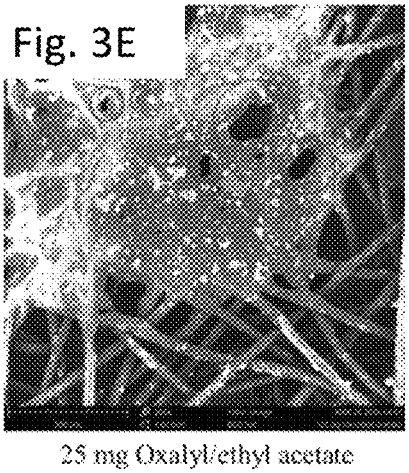
25 mg Oxalyl/ethyl acetate Bacterial growth Untreated PP $2X10^5$ spores PP activated with 10%
poly(melamine-*co*-oxalyl)
no chlorination
$2X10^5$ spores PP activated with 10%
poly(melamine-*co*-oxalyl)
One week post chlorination
$2X10^5$ spores PP activated with 10%
poly(melamine-*co*-oxalyl)
3 months post chlorination
$2X10^4$ spores Non Treated SMS PP 2 months
post treatment
2X10$^5$ spores/coupon 1 week
post treatment
2X10$^5$ spores/coupon

POLY (MELAMINE-CO-OXALYL), METHODS OF SYNTHESIZING AND USING SAME AND ARTICLES TREATED WITH SAME

CROSS REFERENCE TO RELATED APPLICATIONS

This application claims the benefit according 35 U.S.C. § 371 of PCT application IL2021/050974 filed on Aug. 10, 2021 which claimed priority according to 35 U.S.C. § 119 (a) from Israeli application IL 276822 filed on Aug. 19, 2020; each of these earlier applications having the same title and applicant as the present application; and each of these earlier applications fully incorporated herein by reference.

FIELD OF THE INVENTION

The invention is in the field of antibacterial preparations. More particularly, the invention relates to novel N-halamines, to processes for their preparation, and to their uses.

BACKGROUND OF THE INVENTION

N-halamines are characterized by a halogen-nitrogen bond formed by the reaction of amines, amides or imides with halogen, hypohalous acid or hypohalite.

N-halamines exhibit oxidative properties, similar to hypohalous acids and salts (e.g. hypochlorite bleach, NaOCl). The most stable N-halamines are chloramines and bromamines, which are used, for example, in the field of water treatment and disinfection.

Halamines have been attached to polymers and textile for potential use as water purification systems (columns, filters) and biocidal coatings.

The N—Cl bond of N-halamine can be regenerated after oxidation of the substrate by hypochlorite wash if the N—Cl is not adjacent to a C—H bond, since elimination might occur, resulting in loss of N—H capable of being chlorinated.

Use of N-halamines for sanitation of pools, spas and water reservoirs, as additives in laundry products and dishwasher detergent, as protection against chemical warfare agents (CWAs) have all been reported.

SUMMARY OF THE INVENTION

A broad aspect of the invention relates to biocidal compositions and their preparation and use.

One aspect of some embodiments of the invention relates to novel poly(melamine-co-oxalyl). Various embodiments of the invention relate to the molecule with varying degrees of chlorination, from unchlorinated to fully chlorinated. It has been now found that novel poly(melamine-co-oxalyl) exhibit excellent antibacterial properties, while at the same time being stable when incorporated in a variety of products, thus affording long-term effective antibacterial activity to those products. For purposes of this specification and the accompanying claims, the term "antibacterial," should be given a broad interpretation and covers, inter alia, viruses and/or fungi and/or spores (fungal and/or bacterial) as well as bacteria.

Another aspect of some embodiments of the invention relates to synthesis methods for poly(melamine-co-oxalyl). In some embodiments the methods use melamine, or chlorinated form(s) of the molecule, as a starting material.

A third aspect of some embodiments of the invention relates to the incorporation of poly(melamine-co-oxalyl) into other products to impart properties of poly(melamine-co-oxalyl) to the product. According to various exemplary embodiments of the invention the products include, but are not limited to, spray formulations, paints, inks, dyes, fabrics (woven and/or non-woven), fiberglass and building materials. Building materials include, but are not limited to grout and cement. Fiberglass includes spin-fiberglass such as is used in air filters.

It will be appreciated that the various aspects described above relate to solution of technical problems associated with providing an organic skeleton which affords favorable incorporation into matrices, while still enabling the active chlorine to be effective.

Alternatively or additionally, it will be appreciated that the various aspects described above relate to solution of technical problems related to providing a high amount of active chlorine per unit weight of a biocidal polymer.

Alternatively or additionally, it will be appreciated that the various aspects described above relate to solution of technical problems related to providing a biocidal polymer with a long shelf life.

Alternatively or additionally, it will be appreciated that the various aspects described above relate to solution of technical problems related to providing a high degree of freedom with respect to chlorination. Poly (melamine-co-oxalyl) can be incorporated prior to chlorination in aqueous media, with subsequent chlorination of a product which has been treated then dried. Poly (melamine-co-oxalyl) can also be applied as an organic solution of the final chlorinated product, for single step activation of a product.

In one aspect, the invention is directed to a polymer comprising:

(a) a plurality of melamine monomers; and (b) at least one oxalyl linker between each pair of said monomers.

In one embodiment said monomers and linkers are connected linearly. According to another embodiment said monomers and linkers are connected in a branched chain. In a further embodiment of the invention said monomers and linkers are connected in a net like fashion.

A polymer according another embodiment of the invention is one in which at least some of triazine rings of said monomers are connected to at least 2 of said oxalyl linkers. In still another embodiment there is provided a polymer wherein at least some of triazine rings of said monomers are connected to 3 of said oxalyl linkers.

Some polymers of the invention comprise chlorine atoms bound to all nitrogen atoms that are not part of a triazine ring. Other polymers of the invention comprise 2 chlorine atoms bound to at least some nitrogen atoms that are bound directly to a triazine ring.

In another aspect the invention is directed to a composition comprising poly(melamine-co-oxalyl). In one embodiment, the composition comprises a solvent in which said poly(melamine-co-oxalyl) is dissolved. Exemplary compositions may be incorporated into a paint, ink or dye and they may be provided, for example, in a spray bottle.

Illustrative embodiments of compositions according to the invention may comprise at least one ingredient selected from the group consisting of additional solvents, diluents, binders, resins, polymers, fillers, pigments, dyes, wetting agents, catalysts, thickeners, stabilizers, emulsifiers, texturizers, adhesion promoters, UV stabilizers, flatteners, and biocides.

In a further aspect the invention is directed to a fabric treated with a composition of the invention.

In another further aspect the invention is directed to an air filter treated with a composition of the invention. In some embodiments the air filter includes spun fiberglass.

In yet another aspect the invention is directed to a compound comprising a plurality of interconnected units according to Formula (I) or Formula (II):

(I)

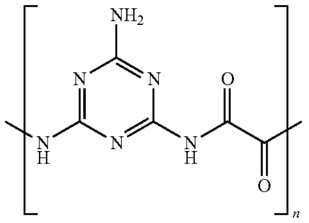

(II)

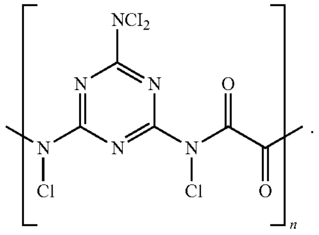

In still another aspect the invention is directed to a compound comprising a plurality of interconnected units according to Formula (III) or Formula (IV):

(III)

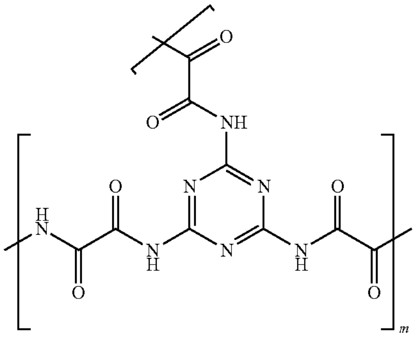

(IV)

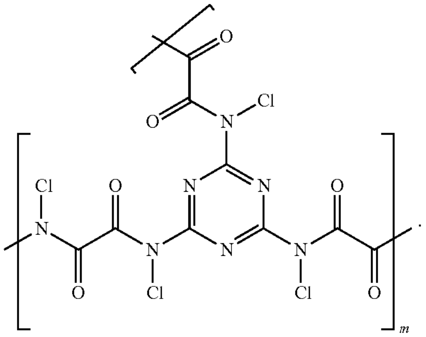

Compounds of the invention can be prepared according to novel synthetic methods, which also form a part of the invention. In one embodiment there is provided a method for producing a compound of Formula (I):

(i)

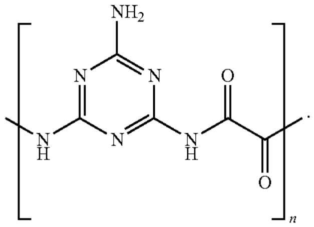

comprising, reacting di-chloromelamine with an acid halide in an organic solvent at 70° C. to 80° C.

In some embodiments the organic solvent comprises carbon tetrachloride and/or toluene, and in others the acid halide comprises oxalyl chloride.

According to one embodiment, the method comprises chlorinating the molecule of Formula (I) to produce a molecule of Formula (II):

(II)

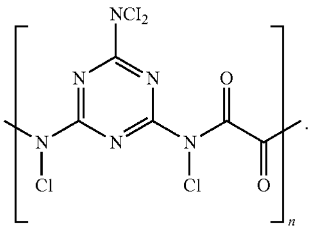

In another embodiment there is provided a method for producing a compound of Formula (III):

(III)

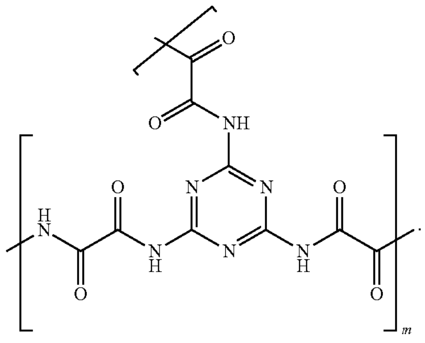

comprising, reacting tri-chloromelamine with an acid halide in an organic solvent at 70° C. to 80° C.

In one embodiment the organic solvent comprises carbon tetrachloride and/or toluene, and in another embodiment the acid halide comprises oxalyl chloride.

According to one embodiment, the method comprises chlorinating a compound of Formula (III) to produce a compound of Formula (IV):

(IV)

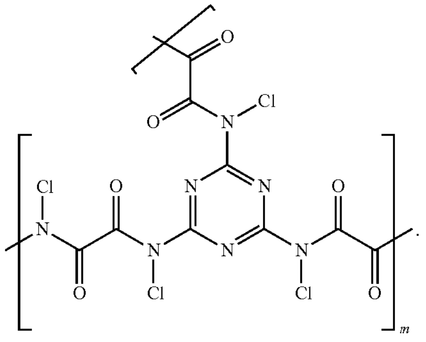

Also encompassed by the invention are articles of manufacture comprising a polymer according to the invention. In one embodiment the polymer is impregnated in the article, and in another embodiment the polymer is located on the surface of the article.

The invention is not limited to any particular article of manufacture. Illustrative and non-limitative examples of articles of manufacture that can benefit from the invention include paints, inks, dyes, fabrics (woven and/or non-woven), polymers, fiberglass, bed sheets, pillowcases, caps, gowns and curtains.

In yet a further aspect, the invention is directed to a method for producing a compound of Formula (III):

(III)

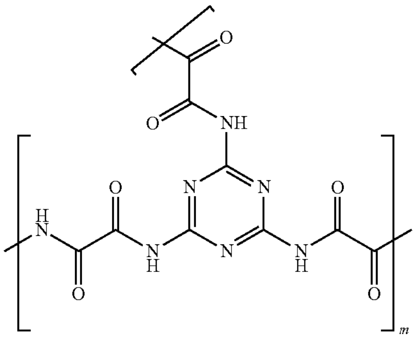

comprising, reacting tri-chloromelamine with an acid halide in an organic solvent at 70° C. to 80° C.

In one embodiment the organic solvent comprises at least one member selected from the group consisting of carbon tetrachloride, chloroform and toluene. In another embodiment acid halide comprises oxalyl chloride.

According to one embodiment, the method comprises chlorinating a compound of Formula (III) to produce a compound of Formula (IV):

(IV)

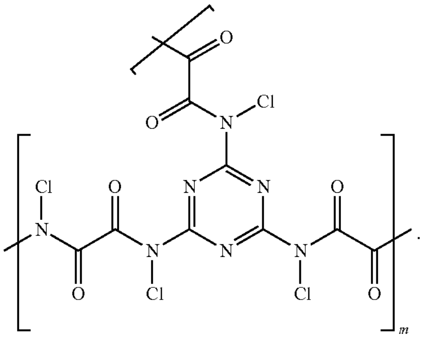

In still a further aspect the invention is directed to a method for producing a compound of Formula (I):

(I)

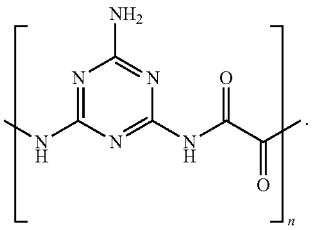

comprising, reacting di-chloromelamine with an acid halide in an organic solvent at 70° C. to 80° C.

In one embodiment the organic solvent comprises at least one member selected from the group consisting of carbon tetrachloride, chloroform and toluene, and in another embodiment the acid halide comprises oxalyl chloride.

According to one embodiment, the method comprises chlorinating a compound of Formula (I) to produce a compound of Formula (II):

(II)

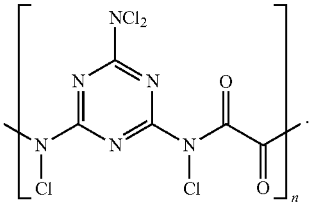

According to another embodiment, the method comprises producing di-chloromelamine by reacting tri-chloromelamine with melamine, water and acetic acid at a temperature of 55° C. to 65° C. In yet another embodiment the method comprises producing di-chloromelamine by reacting tri-chloromelamine with melamine and chloroform at a temperature of 70° C. to 80° C.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments "consist essentially of" and/or "consist of" the recited feature.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The phrase "adapted to" as used in this specification and the accompanying claims imposes additional structural limitations on a previously recited component.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Throughout this application and the accompanying claims percentages (%) of solutions are W/V (weight per volume). All other percentages (%)are W/W (weight per weight) unless otherwise indicated.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar compounds, synthesis steps or parts thereof that appear in more than one figure are generally labeled with the same or similar references in the figures in which they appear. The attached figures are:

FIG. 2A is a photograph of untreated MeltBlown White Oil-only coupon showing significant bacterial growth;

FIG. 2B is a photograph of the activated MeltBlown White Oil-only coupon showing no bacterial growth;

FIG. 2C is a photograph of the untreated Ultraclean™ Blue Poly-backed-Gray Maintenance coupon showing significant bacterial growth;

FIG. 2D is a photograph of the activated Ultraclean™ Blue Poly-backed-Gray Maintenance coupon showing no bacterial growth;

FIG. 3A is a scanning electron micrograph (SEM) of non-woven fabric treated with a polymer solution according to an exemplary embodiment of the invention;

FIG. 3B is a scanning electron micrograph (SEM) of non-woven fabric treated with a polymer solution according to an exemplary embodiment of the invention;

FIG. 3C is a scanning electron micrograph (SEM) of non-woven fabric treated with a polymer solution according to an exemplary embodiment of the invention;

FIG. 3D is a scanning electron micrograph (SEM) of non-woven fabric treated with a polymer solution according to an exemplary embodiment of the invention;

FIG. 3E is a scanning electron micrograph (SEM) of non-woven fabric treated with a polymer solution according to an exemplary embodiment of the invention;

Figure 14A:
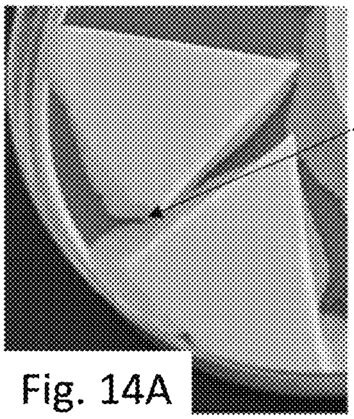
FIG. 14A is a photograph showing growth of *B. anthracis* on untreated polypropylene (PP) following inoculation with $2\times10^5$ spores.
Figure 14B:
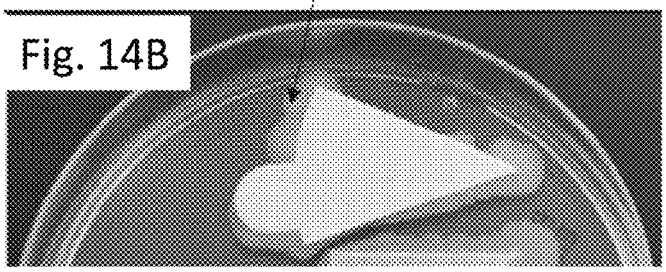
FIG. 14B is a photograph showing growth of *B. anthracis* on PP treated with unchlorinated poly(melamine-co-oxalyl)
Figure 14C:
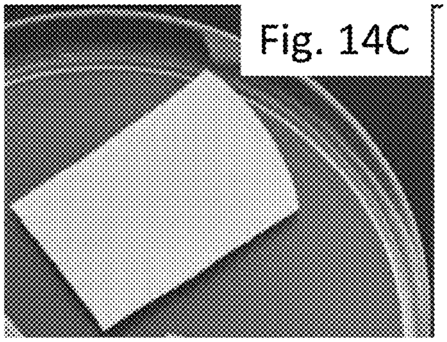
Figure 14D:
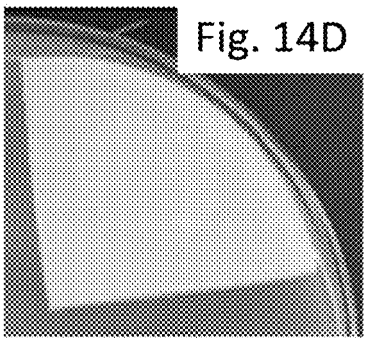
Figure 15A:
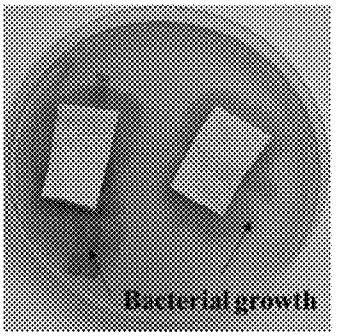
Figure 15B:
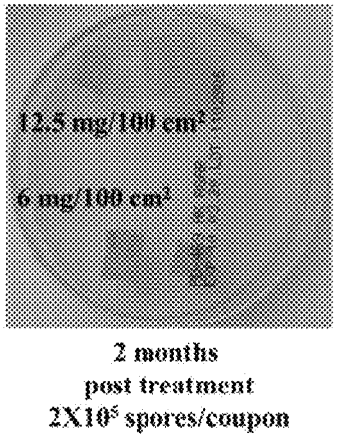
Figure 15C:
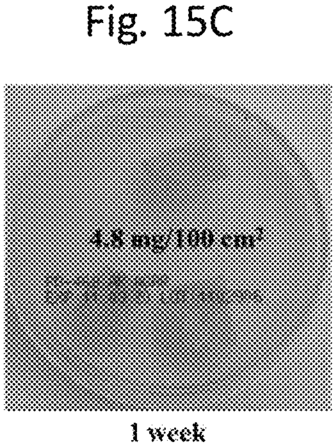
Figure 16:
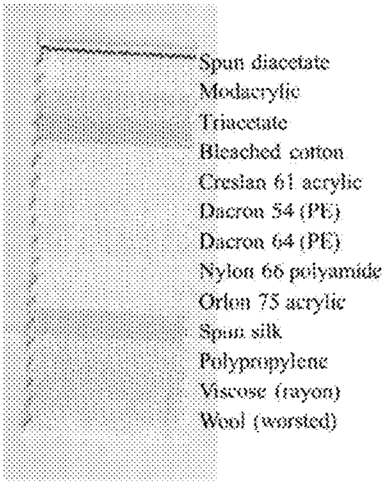
Figure 17A:
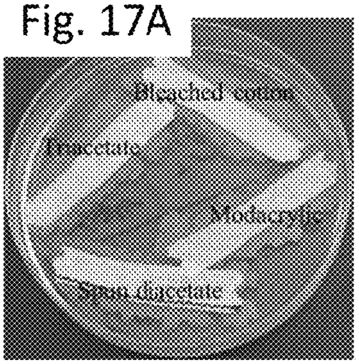
Figure 17B:
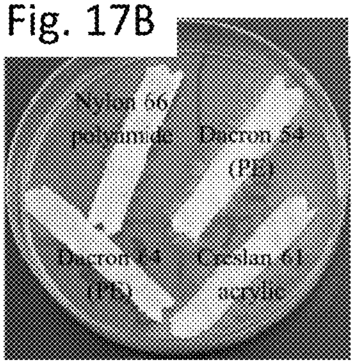
Figure 17C:
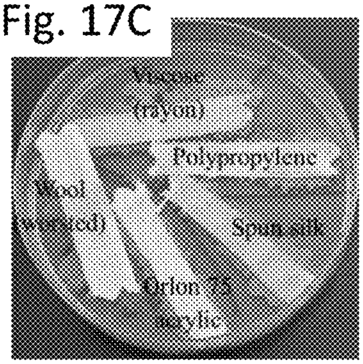
Figure 18A:
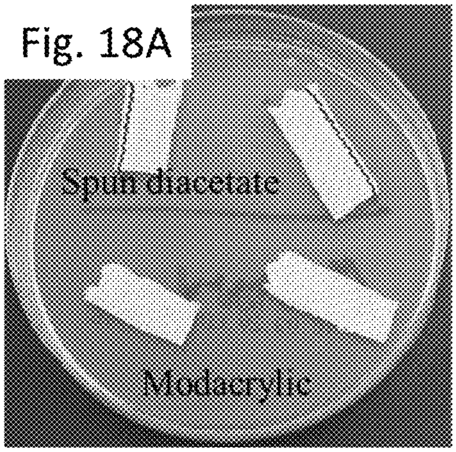
Figure 18B:
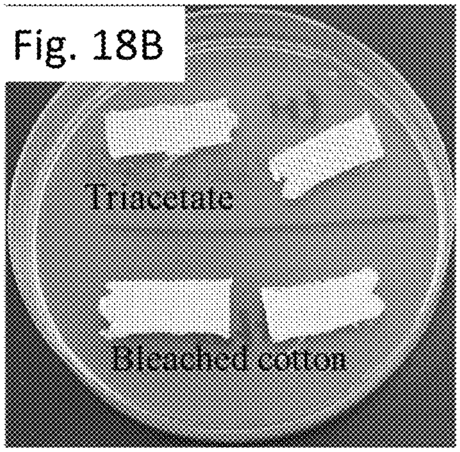
Figure 18C:
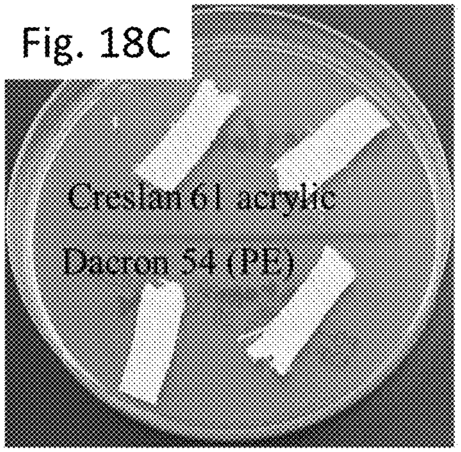
Figure 18D:
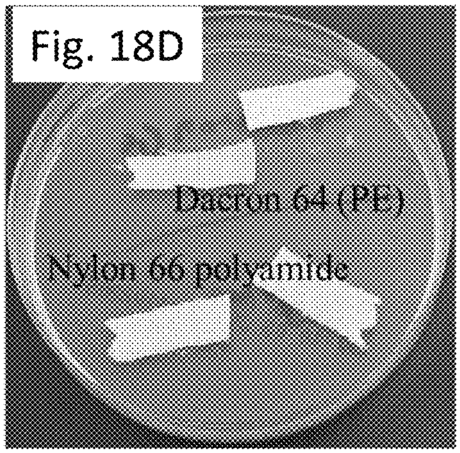
Figure 18E:
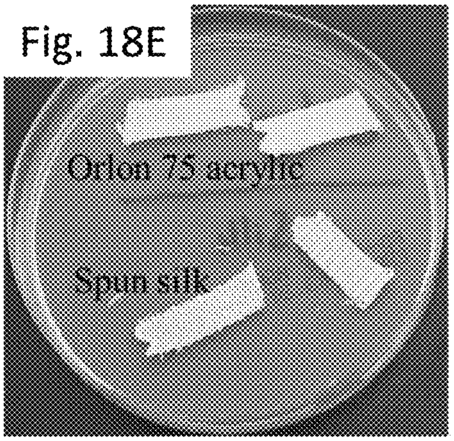
Figure 18F:
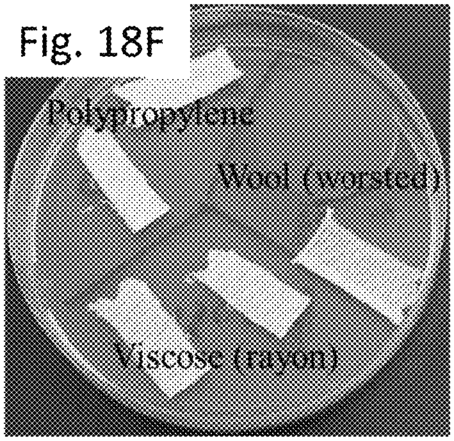

according to an exemplary embodiment of the invention following inoculation with $2\times10^5$ spores;

FIG. 14C is a photograph showing no growth of *B. anthracis* on PP treated with poly(melamine-co-oxalyl) according to an exemplary embodiment of the invention one week post chlorination following inoculation with $2\times10^5$ spores;

FIG. 14D is a photograph showing no growth of *B. anthracis* on PP treated with poly(melamine-co-oxalyl) according to an exemplary embodiment of the invention three months post chlorination following inoculation with $2\times10^4$ spores;

FIG. 15A is a photograph showing growth of *B. anthracis* on untreated Polypropylene SMS non-woven fabric following inoculation with $2\times10^5$ spores;

FIG. 15B is a photograph showing no growth of *B. anthracis* on Polypropylene SMS non-woven fabric treated with 6 mg/100 $cm^2$ or 12.5 mg/100 $cm^2$ chlorinated poly (melamine-co-oxalyl) according to an exemplary embodiment of the invention following inoculation with $2\times10^5$ spores two months post treatment;

FIG. 15C is a photograph showing no growth of *B. anthracis* on Polypropylene SMS non-woven fabric treated with 4.8 mg/100 $cm^2$ chlorinated poly(melamine-co-oxalyl) according to an exemplary embodiment of the invention following inoculation with $2\times10^5$ spores 1 week post treatment;

FIG. 16 is a photograph of a standard multifiber strip (textiles TF MFF 43 (13 fibers), multifiber test fabric, TestFabrics Inc.;

FIG. 17A is a photograph of untreated triacetate, bleached cotton, modacrylic and spun diacetate showing substantial bacterial growth after inoculation with $2\times10^4$ *B. anthracis* spores and incubation for 5 days;

FIG. 17B is a photograph of untreated Nylon 66 polyamide, Dacron 54(PE), Creslan 61 acrylic and Dacron 64 (PE) showing substantial bacterial growth after inoculation with $2\times10^4$ *B. anthracis* spores and incubation for 5 days;

FIG. 17C is a photograph of is a photograph of untreated Viscose (rayon), polypropylene, spin silk, Orlon 75 acrylic and wool (worsted) showing substantial bacterial growth after inoculation with $2\times10^4$ *B. anthracis* spores and incubation for 5 days;

FIG. 18A is a photograph of spun diacetate and modacrylic treated with an acetone solution of poly(tetrachloromelamine-co-oxalyl) according to an exemplary embodiment of the invention showing no bacterial growth after inoculation with $2\times10^4$ *B. anthracis* spores and incubation for 5 days;

FIG. 18B is a photograph of triacetate and bleached cotton treated with an acetone solution of poly(tetrachloromelamine-co-oxalyl) according to an exemplary embodiment of the invention showing no bacterial growth after inoculation with $2\times10^4$ *B. anthracis* spores and incubation for 5 days;

FIG. 18C is a photograph of creslan 61 acrylic and Dacron 54 (PE) treated with an acetone solution of poly(tetrachloromelamine-co-oxalyl) according to an exemplary embodiment of the invention showing no bacterial growth after inoculation with $2\times10^4$ *B. anthracis* spores and incubation for 5 days;

FIG. 18D is a photograph of Dacron 64 (PE) an Nylon 66 treated with an acetone solution of poly(tetrachloromelamine-co-oxalyl) according to an exemplary embodiment of the invention showing no bacterial growth after inoculation with $2\times10^4$ *B. anthracis* spores and incubation for 5 days;

FIG. 18E is a photograph of Orlon 75 acrylic and spin silk treated with an acetone solution of poly(tetrachloromelamine-co-oxalyl) according to an exemplary embodiment of the invention showing no bacterial growth after inoculation with $2\times10^4$ *B. anthracis* spores and incubation for 5 days; and FIG. 18F is a photograph of polypropylene, wool (worsted) and viscose (rayon) treated with an acetone solution of poly(tetrachloromelamine-co-oxalyl) according to an exemplary embodiment of the invention showing no bacterial growth after inoculation with $2\times10^4$ *B. anthracis* spores and incubation for 5 days.

DETAILED DESCRIPTION OF EMBODIMENTS

Embodiments of the invention relate to poly(melamine-co-oxalyl), compositions comprising it, and methods to produce and use it, as well as articles treated with poly (melamine-co-oxalyl).

Specifically, some embodiments of the invention can be used to impart biocidal activity to objects or compositions including for example, but not limited to, paints, inks, dyes, fabrics, polymers, surgical masks, caps, gowns and curtains.

The principles and operation of poly(melamine-co-oxalyl), compositions comprising it and methods to produce and use it according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Exemplary Synthesis Protocols

Figure 1A:
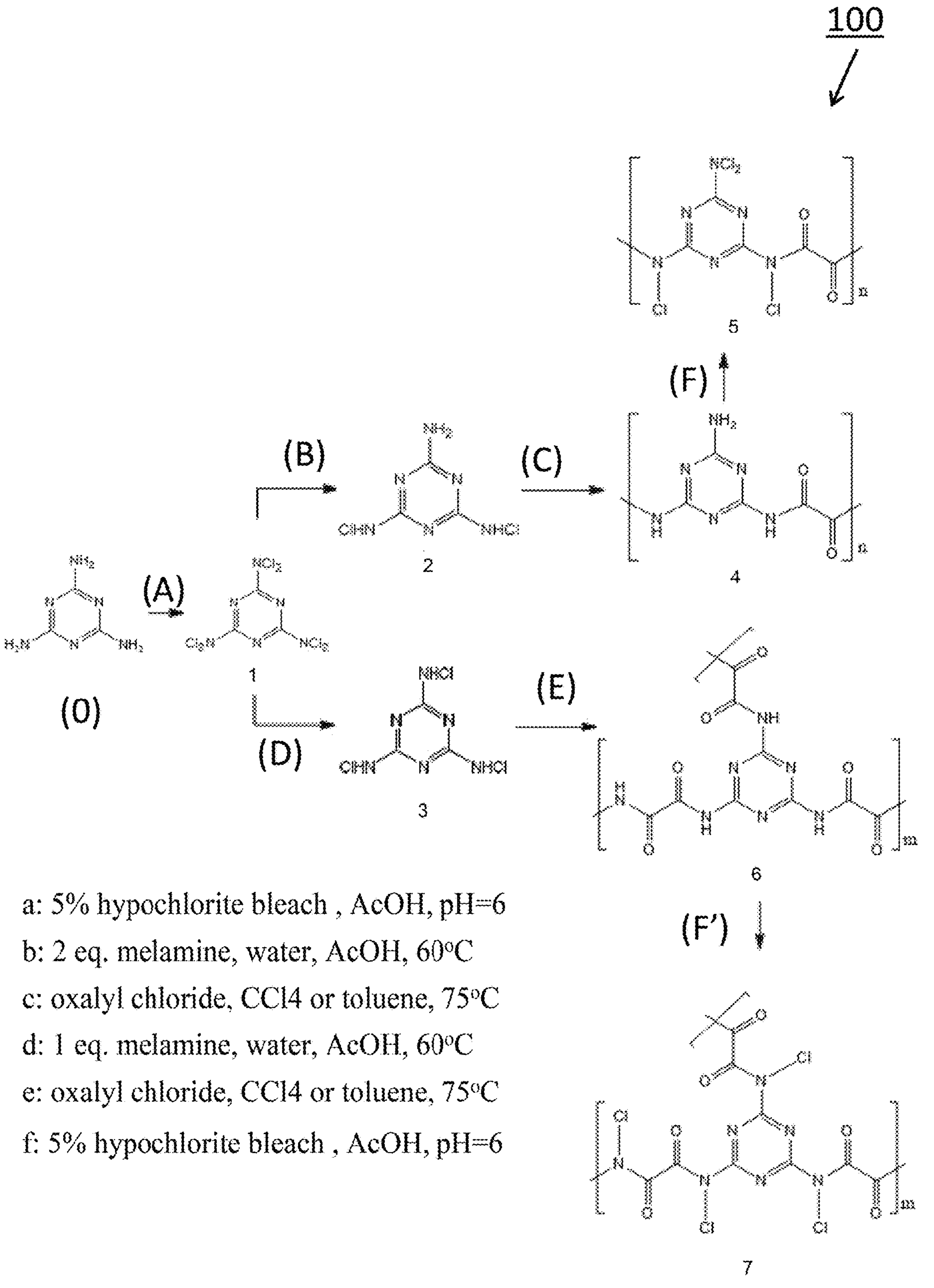
FIG. 1A is a simplified flow diagram of exemplary synthesis protocols according to various exemplary embodiments of the invention.

FIG. 1A is a simplified flow diagram of exemplary synthesis protocols for poly(melamine-co-oxalyl), indicated generally as 100, according to various exemplary embodiments of the invention.

The final poly(melamine-co-oxalyl) synthesis product is generated in either linear polymer form (5) or a net-like highly branched form (7).

In the depicted embodiment, melamine (0), 1,3,5-triazine-2,4,6-triamine, serves as starting material. Melamine (0) was selected as a starting material since the amine groups, of guanidine nature, can also serve as handles for attachment to commercial polymers or polymerizable moieties. Alternatively or additionally, melamine contains three amines which provide potential for 1 to 6 active N—Cl groups. Full chlorination of melamine was carried out using 5% hypochlorite bleach acidified to pH 6 with acetic acid to produce hexachloromelamine (1) which served as a chlorinating agent for further reactions.

Dichloromelamine (2), and trichloromelamine (3) were obtained by disproportionation of chlorine atoms, when hexachloromelamine was mixed and heated with various ratios of melamine in water under slightly acidic conditions (pH 6) at 60° C. Partially chlorinated melamines (2) and/or (3) were used for further conjugation of the melamine moiety as described below.

Preparation of melamine-based polymers, where most of the amine moieties remain available for subsequent chlorination has the potential to produce a highly reactive polymer with up to six chlorine ions per monomer unit. A short linker between melamine groups contributes to a high load of active chlorine per unit weight of polymer. Absence of α-hydrogen atoms makes melamine based polymers amenable to regeneration (e.g. by washing with hypochlorite bleach). Poly(melamine-co-oxalyl), either in a linear form (compounds 4 and 5) or as a crosslinked net (compounds 6 and 7) has all of these features.

Acylation of melamine is usually carried out by prolonged heating with the desired acid anhydride or amide, while acid halides seem to have little or no effect on melamine. The use of high temperatures (170-200° C.), combined with large amounts of acid derivatives (usually serving as solvents), gives rise to mixtures of di- and tri-amides of melamine in many cases.

At (C) and (E) an acid halide (oxalyl chloride) is reacted with di-chloromelamine (2) or tri-chloromelamine (3) respectively in an organic solvent (e.g., carbon tetrachloride or toluene) at 70° C. to 80° C. to form the desired amide (4 or 6 respectively) while releasing $Cl_2$.

As seen at (4) and (6) the reaction of acid halides with chloromelamines produces melamine polymers containing carbonyl groups as linkers between any two melamine moieties.

Specifically, oxalyl chloride was reacted with di-chloromelamine (2) to form linear poly(melamine-co-oxalyl) (4), or with tri-chloromelamine (3) to obtain a net-like highly branched poly(melamine-co-oxalyl) (6).

These polymers were subsequently chlorinated (F and F' respectively) by reacting with 5% hypochlorite bleach in neutral to slightly acidic pH to form polymers (5) and (7) respectively. Polymers (5) and (7) contain a high amount of active chlorine per monomer unit.

Figure 1B:
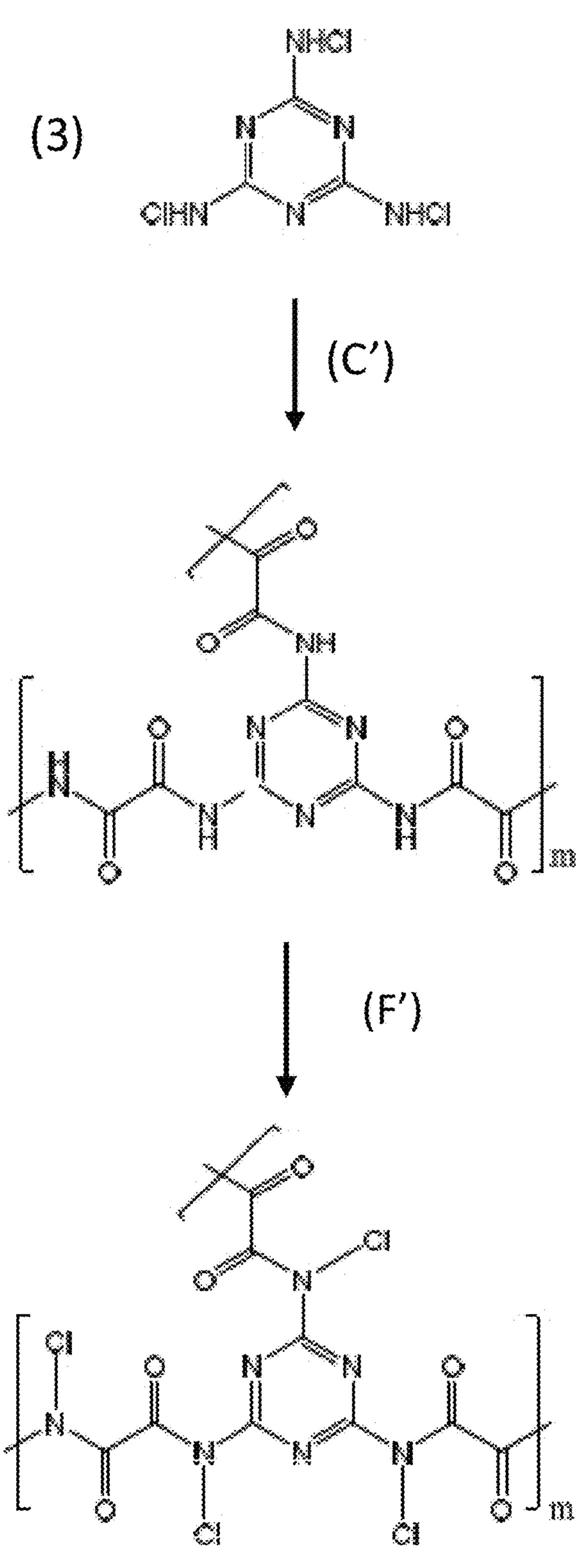
FIG. 1B is a simplified flow diagram of an additional exemplary synthesis protocol according to another exemplary embodiment of the invention.

FIG. 1B is a simplified flow diagram of another exemplary synthesis protocol for poly(melamine-co-oxalyl), indicated generally as 102, according to various exemplary embodiments of the invention.

In the depicted embodiment, tri-chloromelamine (3) serves as a starting material. In the depicted embodiment the starting material is reacted (C') with an acid halide (oxalyl chloride) in an organic solvent (e.g., carbon tetrachloride, chloroform or toluene) at 70° C. to 80° C. to form the desired amide polymer (6) while releasing $Cl_2$.

Polymers of (6) are then chlorinated (F') by reacting with 5% hypochlorite bleach in neutral to slightly acidic pH.

Figure 1C:
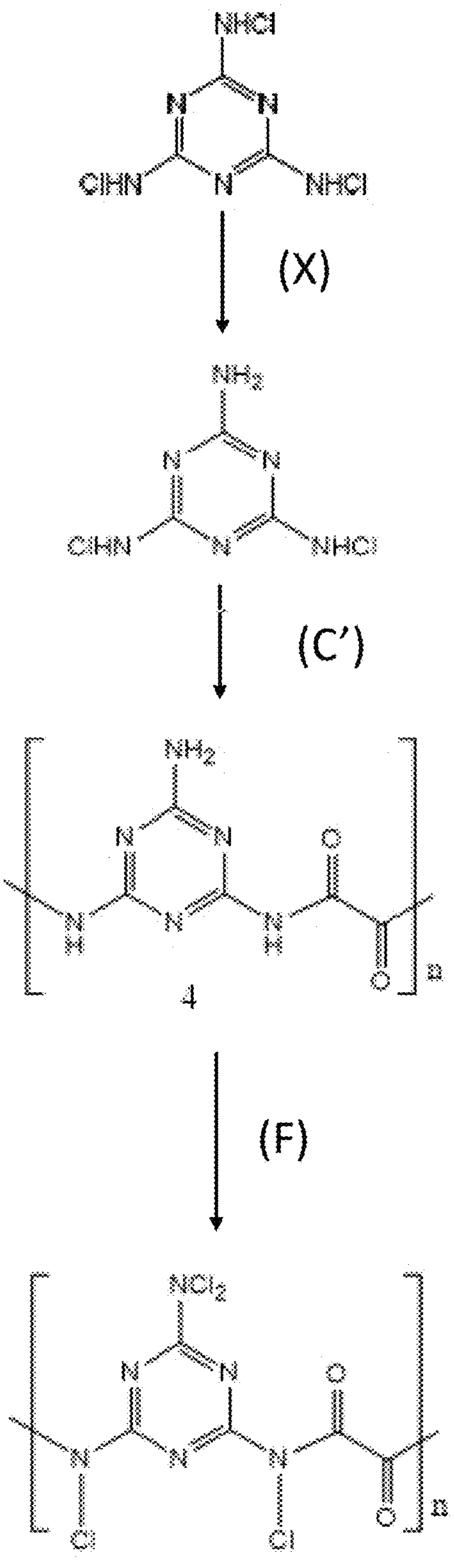
FIG. 1C is a simplified flow diagram of yet another exemplary synthesis protocol for poly(melamine-co-oxalyl), according to various exemplary embodiments of the invention.

FIG. 1C is a simplified flow diagram of yet another exemplary synthesis protocol for poly(melamine-co-oxalyl), indicated generally as 104, according to various exemplary embodiments of the invention.

In the depicted embodiment, di-chloromelamine (2) serves as a starting material. In the depicted embodiment the starting material is reacted (C') with an acid halide (oxalyl chloride) in an organic solvent (e.g., carbon tetrachloride, chloroform or toluene) at 70° C. to 80° C. to form the desired amide polymer (4) while releasing $Cl_2$.

Polymers of (4) are then chlorinated (F) by reacting with 5% hypochlorite bleach in neutral to slightly acidic pH.

Optionally, di-chloromelamine (2) is produced by reacting (X) tri-chloromelamine (3) with melamine in water and acetic acid at 55° C. to 65° C. or with melamine in chloroform at 70° C. to 80° C.

First Exemplary Polymer Definition

Some exemplary embodiments of the invention relate to a polymer including a plurality of melamine monomers and at least one oxalyl linker between each pair of the monomers.

In some embodiments monomers and linkers are connected linearly. According to theses linear embodiments, 2 of the 3 amine groups in a triazine ring of the melamine monomers are substituted with oxalyl.

In some embodiments the monomers and linkers are connected in a branched chain.

In some embodiments the monomers and linkers are connected in a net like fashion. According to these net like embodiments at least some of triazine rings of the monomers are connected to 3 of the oxalyl linkers. Alternatively or additionally, at least some of triazine rings of the monomers are connected to at least 2 of the oxalyl linkers.

Alternatively or additionally, in some embodiments chlorine atoms are bound to all nitrogen atoms that are not part of a triazine ring. According to various exemplary embodiments of the invention 1 or 2 chlorine atoms are bound to each nitrogen atom.

In some embodiments the polymer includes 2 chlorine atoms bound to at least some nitrogen atoms that are bound directly to a triazine ring.

Exemplary Assay

Compounds labelled as 6 in FIG. 1A are detectable by FTIR (Fourier-transform infrared spectroscopy) and NMR (Nuclear magnetic resonance). FTIR and NMR differentiate between NH2, NHCl and NCl.

For these “net-like” polymers of poly(melamine-co-oxalyl):

$^1$H NMR (DMSO-$d_6$): δ 7.83, 8.34 (NH backbone and terminal).

$^{13}$C NMR (DMSO-$d_6$): δ 159.48, 161.14, 161.71.

FTIR-ATR: 3300, 3117, 1633, 1455, 1371, 1173, 977, 785, 573.

The compounds labelled as 4 in FIG. 1A is detectable by FTIR (Fourier-transform infrared spectroscopy) and NMR (Nuclear magnetic resonance). These linear polymers have a different profile from the “net-like polymers:

Linear poly(melamine-co-oxalyl)

$^1$H NMR (DMSO-$d_6$): δ 7.70 (NH).

$^{13}$C NMR (DMSO-$d_6$): δ 159.40.

FTIR-ATR: (three step synthesis; steps A; B and C in FIG. 1A)

3356, 3111, 1651, 1505, 1420, 1158, 1130, 979, 774, 570.

FTIR-ATR: (one-pot synthesis; FIG. 1C)

3309, 3115, 1643, 1494, 1371, 1165, 1007, 775, 573.

The compound labelled as 5 in FIG. 1A is detectable by FTIR (Fourier-transform infrared spectroscopy) and NMR (Nuclear magnetic resonance). The chlorinate linear polymers have a different profile from their unchlorinated counterparts.

Linear poly(tetrachloromelamine-co-oxalyl)

$^{13}$C NMR (Pyridine-ds): 6168.53, 169.12

FTIR-ATR: 1531, 1336, 1096, 787, 680.

SEM-EDAX is a qualitative method useful for determining the existence of polymer-originating chlorine on fabrics or other treated substrates. The chlorine in poly(melamine-co-oxalyl) can be also detected qualitatively be SEM-EDAX (Scanning Electron Microscopy with Energy Dispersive X-Ray Analysis).

When compounds labelled as 6 and 7 in FIG. 1A are sprayed onto a matrix, they are detectable by FTIR by subtraction of the matrix spectrum from the treated matrix spectrum.

Chlorine on can also be analyzed by FTIR, as the pattern for melamine, acylated melamine and chlorinated melamine moieties is easily determined by FTIR. Identification by FTIR involves comparison to a parent compound, starting material or a previous batch of polymer.

Exemplary Compositions

Some exemplary embodiments of the invention relate to a composition including poly(melamine-co-oxalyl). In some embodiments the composition includes a solvent in which the poly(melamine-co-oxalyl) is dissolved. In some embodiments the dissolved polymer in solvent is incorporated into a paint, ink or dye. In some embodiments a surface (e.g. a wall) is treated with a paint containing poly(melamine-co-oxalyl). The poly(melamine-co-oxalyl) can be chlorinated after the paint dries by spraying with a solution of bleach or wiping with a sponge soaked in bleach. In some embodiments the composition takes the form of a building material such as plaster, dry-wall, grout, cement masterbatch or plastic. According to these embodiments poly(melamine-co-oxalyl) is added as a solid and/or in solution.

In some embodiments the dissolved polymer in solvent is provided in a spray bottle or other spraying device.

Alternatively or additionally, in some embodiments the composition includes at least one ingredient selected from the group consisting of additional solvents, diluents, binders, resins, polymers, fillers, pigments, dyes, wetting agents, catalysts, thickeners, stabilizers, emulsifiers, texturizers, adhesion promoters, UV stabilizers, flatteners, crosslinkers and biocides.

In some exemplary embodiments of the invention, a fabric treated with a composition as set forth above acquires properties of the polymer. According to various exemplary embodiments of the invention the fabric is a non-woven fabric or a woven fabric. According to various exemplary embodiments of the invention useful article of manufacture including, but not limited to, surgical masks and/or caps/gowns and/or curtains are fashioned from the treated fabric. In some embodiments these useful items acquire the properties of the polymer used to treat the fabric.

Second Exemplary Polymer Definition

Some exemplary embodiments of the invention relate to a compound including a plurality of interconnected units according to Formula (I) or Formula (II):

(I)

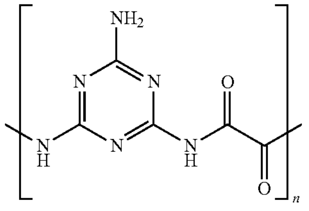

(II)

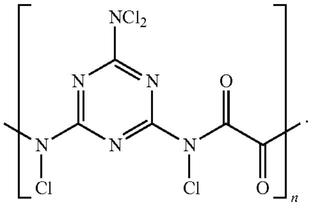

Third Exemplary Polymer Definition

Some exemplary embodiments of the invention relate to a compound including a plurality of interconnected units according to Formula (III) or Formula (IV):

(III)

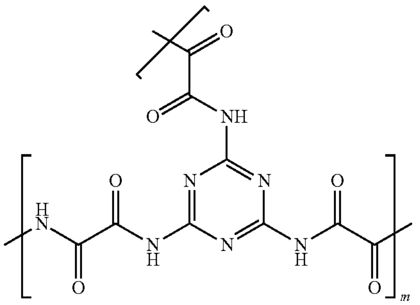

(IV)

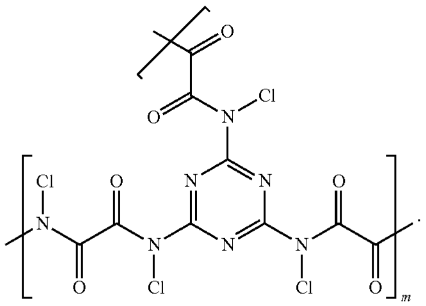

First Exemplary Synthesis Method

Some exemplary embodiments of the invention relate to a method including, reacting di-chloromelamine with an acid halide in an organic solvent at 70° C. to 80° C. to produce a molecule according to Formula(I):

(I)

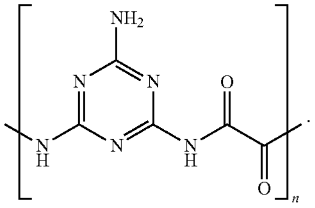

In some embodiments the organic solvent includes carbon tetrachloride and/or toluene. Alternatively or additionally, in some embodiments the acid halide includes oxalyl chloride.

In some embodiments the method includes chlorinating the molecule according to Formula(I) to produce a molecule according to Formula (II):

(II)

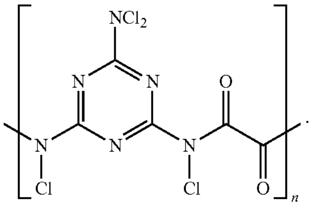

Second Exemplary Synthesis Method

Some exemplary embodiments of the invention relate to a method including, reacting tri-chloromelamine with an acid halide in an organic solvent at 70° C. to 80° C. to produce a molecule according to Formula(III):

(III)

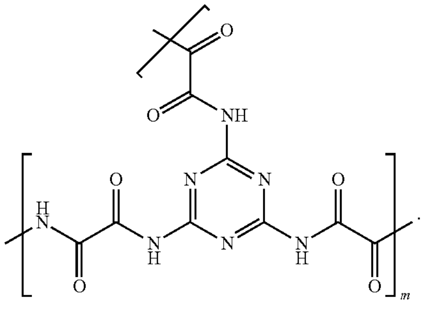

In some embodiments the organic solvent includes carbon tetrachloride and/or toluene. Alternatively or additionally, in some embodiments the acid halide includes oxalyl chloride.

Alternatively or additionally, in some embodiments the method includes chlorinating the molecule according to Formula (III) to produce a molecule according to Formula (IV):

(IV)

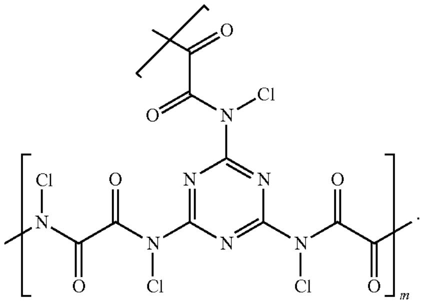

Additional Exemplary Synthesis Protocol

FIG. 1B is a simplified flow diagram of an additional exemplary synthesis protocol, indicated generally as 102, according to another exemplary embodiment of the invention. In the depicted embodiment, synthesis protocol 102 includes reacting (C') tri-chloromelamine (3) with an acid halide in an organic solvent at 70° C. to 80° C. to produce a molecule according to Formula (III):

(III)

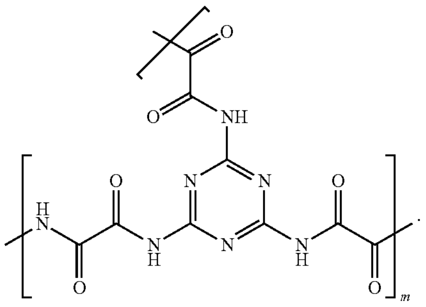

The molecule of formula (III) is labeled (6) in FIG. 1B.

According to various exemplary embodiments of the invention organic solvent includes carbon tetrachloride and/or chloroform and/or toluene. Alternatively or additionally, the acid halide includes oxalyl chloride.

In the depicted embodiment, method 102 includes chlorinating (F') the molecule according to Formula (III) to produce a molecule according to Formula (IV):

(IV)

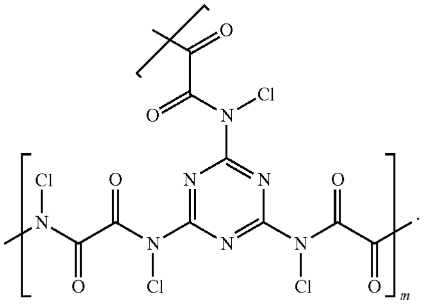

The molecule of formula (IV) is labeled (7) in FIG. 1B.

In some exemplary embodiments of the invention, chlorination at (F') employs 5% hypochlorite bleach plus acetic acid at pH 6.

Further Additional Exemplary Synthesis Protocol

FIG. 1C is a simplified flow diagram of an additional exemplary synthesis protocol, indicated generally as 104, according to another exemplary embodiment of the invention. Depicted exemplary protocol 104 includes reacting (C') di-chloromelamine (3) with an acid halide in an organic solvent at 70° C. to 80° C. to produce a molecule according to Formula (I):

(I)

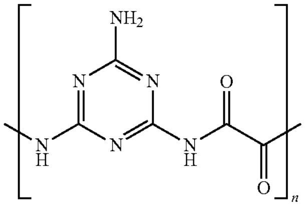

The molecule according to Formula (I) is labelled (4) in the figure.

According to various exemplary embodiments of the invention the organic solvent includes carbon tetrachloride and/or chloroform and/or toluene. Alternatively or additionally, in some embodiments the acid halide includes oxalyl chloride. Depicted exemplary protocol 104 includes chlorinating (F) the molecule according to Formula(I) to produce a molecule according to Formula (II):

(II)

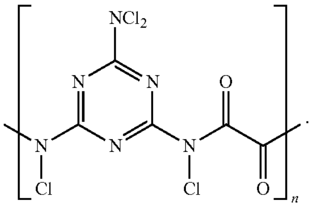

The molecule according to Formula (II) is labelled (5) in the figure. In some exemplary embodiments of the invention, chlorination at (F) employs 5% hypochlorite bleach plus acetic acid at pH 6.

In the depicted embodiment, synthesis protocol 105 includes producing the di-chloromelamine by reacting tri-chloromelamine with:

(A) melamine, water and acetic acid at 60° C.; or (B) melamine and chloroform at 75° C.

In some exemplary embodiments of the invention there is provided a method of producing di-chloromelamine comprising: reacting tri-chloromelamine with melamine in water and acetic acid at 55° C. to 65° C.

In some exemplary embodiments of the invention there is provided a method of producing di-chloromelamine comprising: reacting tri-chloromelamine with melamine in chloroform at 70° C. to 80° C.

Exemplary Articles of Manufacture

In some exemplary embodiments of the invention there is provided an article of manufacture comprising a compound as depicted in FIG. 1 A at 4 and/or 5 and/or 6 and/or 7. As described hereinabove, such compounds have antibacterial properties. In some embodiments the compound is impregnated in the article.

Alternatively or additionally, in some embodiments the compound is located on the surface of the article. In some embodiments the article of manufacture is selected from the group consisting of paints, inks, dyes, fabrics, woven and non-woven, polymers, surgical masks, caps, gowns and curtains.

It is expected that during the life of this patent many suitable reaction protocols will be developed and the scope of the invention is intended to include all such new technologies a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Alternatively, or additionally, features used to describe a method can be used to characterize composition or polymer and features used to describe a composition or polymer can be used to characterize a method.

It should be further understood that the individual features described hereinabove can be combined in all possible combinations and sub-combinations to produce additional embodiments of the invention. The examples given above are exemplary in nature and do not limit the scope of the invention which is defined solely by the following claims.

Each recitation of an embodiment of the invention that includes a specific feature, part, component, module or process is an explicit statement that additional embodiments of the invention not including the recited feature, part, component, module or process exist.

Alternatively or additionally, various exemplary embodiments of the invention exclude any specific feature, part, component, module, process or element which is not specifically disclosed herein.

Specifically, the invention has been described in the context of certain use scenarios but might also be used in a wide variety of additional use scenarios.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms “include”, and “have” and their conjugates as used herein mean “including but not necessarily limited to”.

Additional objects, advantages, and novel features of various embodiments of the invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Example 1

Activation of Sorbent Fabrics

Commercial sorbent fabrics, used for the collection of chemical spills, were activated by linear poly(melamine-co-oxalyl) according to an embodiment of the invention (see molecule 4 in FIG. 1A).

Two characteristic sorbent fabric sheets were selected:

MeltBlown White Oil-only (sorbent media, 100% polypropylene, Evolution Sorbent Products UK, Limited); and Ultraclean™ Blue Poly-backed-Gray Maintenance (sorbent media, 75% Synthetic Fibers, 20% Polypropylene, 3% Polyethylene, 1% Boric Acid, 1% Proprietary Additives, Evolution Sorbent Products UK, Limited).

Pieces of the sorbent fabric sheets were cut into coupons and placed in emulsions of poly(melamine-co-oxalyl) in ethanol (0.1M and 0.025M) for 2 minutes, the excess was removed and the fabric coupons let to dry. Later, the fabric coupons were immersed in neutral 5% hypochlorite bleach for 30 seconds, excess removed, washed with water, excess removed and dried.

Activated sorbent fabrics were tested for VX decontamination and anthrax spores neutralization as described below.

Example 2

CWA Decontamination by Poly(melamine-co-oxalyl) Activated Sorbent Fabrics

In order to evaluate the ability of Poly(melamine-co-oxalyl) on sorbent fabric to decontaminate VX (O-ethyl-S-2-(N,N-diisopropylamino)ethyl methylphosphonate) by solid state magic angle spinning (MAS) 31P NMR was used for evaluation (Mizrahi et al. (2005) Environ. Sci. Tech. 39: 8931-8935; fully incorporated herein by reference). In a typical test, the activated sorbent fabric (30-50 mg, 3 weeks post chlorination) was used to fill a 4-mm ZrO2 rotor. Next, VX (1 mg) was applied directly to the center of the sample. The rotor was sealed with a fitted Kel-F cap. 31P MAS NMR experiments were carried out on a 500 MHz Avance (Bruker) spectrometer equipped with a 4-mm standard CP-MAS probe using direct excitation (no CP). The observation frequency was 202 MHz (31P). Remaining VX quantity and decontamination products were determined.

Activated MeltBlown White Oil-only showed complete decontamination of VX within 12 days, with a major oxidized-VX product, which gradually hydrolyzed to non-toxic EMPA (ethyl methylphosphonic acid) over the next 50 days. Activated Ultraclean™ Blue Poly-backed-Gray Maintenance completely decontaminated VX within 5 hours, leading to the same products and timeline as above. In comparison, no VX was decontaminated on both non-activated sorbent fabrics.

These results indicate that a polymer according to an exemplary embodiment of the invention imparts CWA decontamination capability to a fabric treated with it.

Example 3

Anthrax Spores Disinfection by Poly(melamine-co-oxalyl) Activated Sorbent Fabrics Activated and naïve sorbent fabrics were cut into 1.5×1.5 $cm^2$ coupons and contaminated with a solution containing $4\times10^4$ *B. anthracis* spores on each coupon. The same polymer as in Examples 1 and 2 was employed for activation. The coupons were left to dry for 24 h and were transferred into petri dishes containing Tryptose agar medium. The dishes were incubated in 37° C. for 7 days and bacterial growth was monitored. FIG. 2 shows that activated sorbent fabrics showed complete bacterial kill, while naïve coupons showed abundant bacterial growth.

FIG. 2A shows the Untreated MeltBlown White Oil-only coupon and FIG. 2B shows the Activated MeltBlown White Oil-only coupon.

FIG. 2C shows the Untreated Ultraclean™ Blue Poly-backed-Gray Maintenance coupon and FIG. 2D shows the Activated Ultraclean™ Blue Poly-backed-Gray Maintenance coupon.

These results clearly demonstrate that a polymer according to an exemplary embodiment of the invention imparts antibacterial properties to a fabric treated with it.

Example 4

Anthrax Spores Disinfection by Poly(melamine-co-oxalyl) Containing PP Plastic

A master batch of 10% Poly(melamine-co-oxalyl) in polypropylene was prepared. Using this master batch, coupons of polypropylene containing 5% or 10% poly(melamine-co-oxalyl) were prepared, as models for drain systems. The coupons were chlorinated by neutral 5% hypochlorite bleach/NaDCC tablets/gelled bleach, by means of immersion for 3 hours. Subsequently, the coupons were washed with water, immersed in a water bath and dried.

Linear polymer (i.e. 4 in FIG. 1A) was fabricated in PP (polypropylene) as a 10% masterbatch. The masterbatch was used to create 10% and 5% additive-containing PP plastic coupons.

Activated and naïve plastic coupons were contaminated with a solution containing either $2\times10^4$ or $2\times10^5$ *B. anthracis* spores on each coupon. Activated coupons were contaminated either one week or 3 months post chlorination. The coupons were left to dry for 24 h and were transferred into petri dishes containing Tryptose agar medium. The dishes were incubated in 37° C. for 7 days and bacterial growth was monitored. The activated sorbent fabrics showed complete bacterial kill, while naïve coupons showed abundant bacterial growth. Treated plastic coupons showed little to no bacterial growth, while original coupons and activated coupons without chlorination, showed large bacterial growth.

FIG. 14A is a photograph showing growth of *B. anthracis* on untreated polypropylene (PP) following inoculation with $2\times10^5$ spores.

FIG. 14B is a photograph showing growth of *B. anthracis* on PP treated with unchlorinated poly(melamine-co-oxalyl) according to an exemplary embodiment of the invention following inoculation with $2\times10^5$ spores.

FIG. 14C is a photograph showing no growth of *B. anthracis* on PP treated with poly(melamine-co-oxalyl) according to an exemplary embodiment of the invention one week post chlorination following inoculation with $2\times10^5$ spores.

FIG. 14D is a photograph showing no growth of *B. anthracis* on PP treated with poly(melamine-co-oxalyl) according to an exemplary embodiment of the invention three months post chlorination following inoculation with $2\times10^4$ spores.

These results indicate that incorporation of Poly(melamine-co-oxalyl) in conventional plastics can impart antibacterial properties to those plastics for at least three months, but only if the Poly(melamine-co-oxalyl) is chlorinated.

Example 5

Anthrax Spores Disinfection by Poly(melamine-co-oxalyl) Sprayed PP Non-Woven Fabric In order to determine whether chlorinated poly(melamine-co-oxalyl) could be used directly to protect a substrate, polypropylene fibers were activated with chlorinated poly (melamine-co-oxalyl), instead of immersion in non-chlorinated polymer, followed by subsequent chlorination by immersion in chlorine solutions as in previous examples.

Polypropylene SMS non-woven fabric was directly sprayed with an acetone solution of chlorinated poly(tetrachloromelamine-co-oxalyl) to quickly activate fabric and make it ready ready to use.

Polypropylene SMS non-woven fabric (ca. 200 $cm^2$) was sprayed with 0.5 mL acetone containing 10-25 mg poly (tetrachloromelamine-co-oxalyl) via airbrush. The fabric was cut into 2.25 $cm^2$ pieces which were contaminated with $2\times10^5$ *B. anthracis* spores each.

The fabric samples were left to dry for 24 h and were transferred into petri dishes containing Tryptose agar medium. The dishes were incubated in 37° C. for 7 days and bacterial growth was monitored.

The non-woven polypropylene fabrics were either newly-activated, 2 months post spray activation or untreated (control). No bacterial growth was evident on any treated fabric, regardless of active polymer concentration, as opposed to the non-treated fabric that showed high bacterial growth.

FIG. 15A is a photograph showing growth of *B. anthracis* on untreated Polypropylene SMS non-woven fabric following inoculation with $2\times10^5$ spores.

FIG. 15B is a photograph showing no growth of *B. anthracis* on Polypropylene SMS non-woven fabric treated with 6 mg/100 $cm^2$ or 12.5 mg/100 $cm^2$ chlorinated poly (melamine-co-oxalyl) according to an exemplary embodiment of the invention following inoculation with $2\times10^5$ spores two months post treatment.

FIG. 15C is a photograph showing no growth of *B. anthracis* on Polypropylene SMS non-woven fabric treated with 4.8 mg/100 $cm^2$ chlorinated poly(melamine-co-oxalyl)

according to an exemplary embodiment of the invention following inoculation with $2\times10^5$ spores 1 week post treatment.

This example demonstrates that chlorinated poly(tetrachloromelamine-co-oxalyl) can be used directly to activate fabric in a single step.

Example 6

Anthrax Spores Disinfection By Poly(melamine-co-oxalyl) Sprayed Textile

A standard multifiber strip (textiles TF MFF 43 (13 fibers), multifiber test fabric, TestFabrics Inc.; depicted in FIG. 16) was activated by directly spraying with an acetone solution of poly(tetrachloromelamine-co-oxalyl) from an airbrush (10 mg total on whole strip) as in example 5. The fine aerosol quickly dried and the multifiber was cut to separate the different fabrics.

Fabric pieces (both untreated and sprayed) were contaminated with $2\times10^4$ *B. anthracis* spores each. The fabric samples were left to dry for 24 h and were transferred into petri dishes containing Tryptose agar medium.

The dishes were incubated in 37° C. for 5 days and bacterial growth was monitored. No bacterial growth was evident on any treated fabric (FIG. 18A; FIG. 18B; FIG. 18C; FIG. 18*d*; FIG. 18E and FIG. 18F). In sharp contrast, all non-treated fabrics showed significant bacterial growth (FIG. 17A; FIG. 17B and FIG. 17C).

This example demonstrates that poly(tetrachloromelamine-co-oxalyl) according to an exemplary embodiment of the invention imparts ant-bacterial properties to spun diacetate, modacrylic, triacetate, bleached cotton, creslan 61 acrylic, Dacron 54 (PE), Dacron 64 (PE) nylon 66 polyamiode, orlon 75 acrylic, spun silk, polypropylene, viscose (rayon) and wool (worsted).

Examples 1 through 6 taken together demonstrate that chlorinated polymers according to various exemplary embodiments of the invention can be incorporated in and/or applied to textiles (woven), non-woven fabrics, plastics, paints, coatings, sealants, grout and silicone-based materials to impart anti-bacterial and/or anti CWA properties to those materials. In some embodiments chlorinated polymers according to various exemplary embodiments of the invention are applied directly. In other exemplary embodiments of the invention, polymers according to various exemplary embodiments of the invention are applied first and subsequently chlorinated.

Evaluation of antiviral effects using herpes simplex in experiments similar to Examples 1-6 showed that chlorinated poly(melamine-co-oxalyl) also has anti-viral activity (data not shown).

Example 7

Use in Layered Articles

An additional series of experiments was conducted in order to determine the suitability and efficacy of chlorinated poly(melamine-co-oxalyl) in the context of layered articles, as may be for instance wearable products, bed sheets, pillow cases, etc.

The article tested was made of PP (polypropylene) in three layers: spunlaid—meltblown—spunlaid (SMS). The color on the external layer serves as a reminder for the user to not change sides during multiple uses so as to keep the internal layer next to the skin.

In order to reduce the effect of chlorinated poly(melamine-co-oxalyl) on the person using the layered article, while enhancing the protection against bacteria and viruses in the environment, the chlorinated poly(melamine-co-oxalyl) should be in or on the external layer of the article.

For this reason, it was decided to spray the external layer of the article with poly(tetrachloromelamine-co-oxalyl) as in Example 6.

In this case, the solvent for the chlorinated additive solution was chosen for rapid evaporation and compatibility with human skin (in case such spraying will take place shortly before use). For safety reasons, solutions of 0.5-1% were tested. Water was not a suitable solvent, as the external layer of the article was hydrophobic, in order to repel droplets. 0.5% and 1% solutions of four chlorinated additives (DM-4212-78; DM-4212-65; DM-4664-65 and DM-11-0201-37) were prepared in three organic solvents (ethanol, ethyl acetate and acetone). Each of these solvents has a low boiling point and a high biocompatibility. In addition, two additives from the fragrance industry (DEP and BB) were tested, in case they were needed to enhance dissolution and/or dispersion on PP.

Dissolution was tested visually and active chlorine was measured qualitatively using KI-starch paper (Supelco item 37215), over five days. Results are summarized in Table 1.

TABLE 1 solubility and Cl activity over time for chlorinated poly(melamine-co-oxalyl) in different solvents

| | Ox-Cl DM-4212-78 | | | | T-Cl DM-4212-65 | | | |
|---|---|---|---|---|---|---|---|---|
| | 0.5% | | 1% | | 0.5% | | 1% | |
| Solvent | solution | Cl | solution | Cl | solution | Cl | solution | Cl |
| DEP | −/+ | 72 h | −/+ | 66 h | + | 72 h | + | 66 h |
| BB | + | 72 h | + | 66 h | + | 72 h | + | 66 h |
| EA | + | 5 days | + | 5 days | + | 5 days | + | 5 days |
| A | + | 5 days | + | 5 days | + | 5 days | + | 5 days |
| E | + | 2 h | | | + | 30 min | | |

TABLE 1-continued solubility and Cl activity over time for chlorinated poly(melamine-co-oxalyl) in different solvents

| | BA-Cl DM-4664-65 | | | | U-Cl DM-11-0201-37 | | | |
|---|---|---|---|---|---|---|---|---|
| | 0.5% | | 1% | | 0.5% | | 1% | |
| Solvent | solution | Cl | solution | Cl | solution | Cl | solution | Cl |
| DEP | + | 72 h | + | 66 h | + | 72 h | + | 66 h |
| BB | + | 72 h | + | 66 h | + | 72 h | + | 66 h |
| EA | + | 5 days | + | 5 days | + | 5 days | + | 5 days |
| A | + | 5 days | + | 5 days | + | 5 days | + | 5 days |
| E | + | | | | + | 30 min | | |

DEP = diethyl phthalate;
BB = benzyl benzoate;
EA = ethyl acetate;
A = acetone;
E = ethanol Table 1 shows that ethanol is not a suitable solvent, as it is oxidized by the active chlorine of the additives, and uses them up within 30 minutes to 2 hours. All the other solutions were stable over 5 days. There seemed to be no need for the addition of diethyl phthalate or benzyl benzoate, since the solutions in acetone and ethyl acetate were clear and stable.

OX CL DM-4212-78 is [poly(tetrachloromelamine-co-oxalyl)] according to an exemplary embodiment of the invention.

T-CL DM-4212-65 is chlorinated trimelamine benzene tricarboxamide which served as a positive control.

Example 8

Exemplary Spray Activation of Articles

In order to assay promising solutions from Example 7, Solutions of T-Cl DM 4212-65 and Ox-Cl DM 4212-78 in acetone and ethyl acetate were sprayed from an airbrush unto the colored outer layer of the article of Example 7. Final amounts of additives on the article were 12.5 mg and 25 mg respectively distributed over the approximately 200 $cm^2$ surface of the article. The fine spray resulted in rapid evaporation of the solvents. The external layer of the article had a faint odor of halamine (similar to pool water), for a short time post spraying.

The existence of active chlorine on the external layer of the article was determined by placing a drop of KI-starch solution on its surface. The aqueous drop remained on the surface, due to hydrophobicity of the PP. Immediately after application, the drop turned yellow-orange as a result of the reaction with iodine, while dark purple-black precipitate formed, as a result of the reaction with starch. This effect was evident without change for more than 2 months (on-going) on sprayed articles at room temperature without any cover. The reaction of chlorine with iodine turns chlorine into chloride (Cl—) and iodide (I—) into iodine that colors the aqueous drop and turns it yellow. Meanwhile, the starch also reacts to form a dark purple precipitate.

Placing a drop of KI-starch solution onto the inner layer of the article produced no coloring of the drop and no formation of dark precipitate.

These results suggest that aqueous droplets containing microorganisms will behave in a similar manner: remain for an extended period of time on the external layer, while active chlorine is extracted from the treated outer layer of the article into the droplet, oxidizing the microorganisms.

Example 9

SEM Evaluation of Treated Layered Articles

In order to evaluate different modes of spray application of solutions from Example 7 with respect to article external layer coverage by the active additives SEM (Phenom ProX, Phenom, The Netherlands) evaluation was performed.

Small samples of the sprayed external layer were placed onto double-sided adhesive carbon film on specimen mounts, and examined at 10 Kv. Tested articles were sprayed by 4 solutions: compounds T-Cl DM 4212-65 and Ox-Cl DM 4212-78 (from Example 7), in either acetone or ethyl acetate and in the amount of 12.5 mg or 25 mg per article. The specimens were examined for tears in the PP layer, blocking of the spaces between fibers and overall coverage.

FIG. 3A, FIG. 3B, FIG. 3C, FIG. 3D and FIG. 3E, show the different coatings and their influence on the PP layer. Ruptures in the PP layer are indicated by red circles (FIGS. 3D and 3E).

These results indicate that ethyl acetate solutions of a polymer according to an embodiment of the invention tend to form small ruptures in the PP fibers, while the additive T-Cl DM 4212-65 (chlorinated trimelamineamide benzoate) formed clusters, which, at higher concentrations (25 mg per article), partially blocked the spaces between fibers.

A method employing Ox-Cl DM 4212-78 [poly(tetrachloromelamine-co-oxalyl)] dissolved in acetone appears suitable to be applied to various layered articles by spraying only the external layer. Using this method, activity is evident for months, no active chlorine is present on the inner layer, and sufficient coverage of the outer PP layer of the article is achieved. This method was used in all subsequent examples relating to layered articles.

Example 10

Anti-bacterial Properties of Layered Articles

In order to confirm the results of Examples 1 through 6 in the specific context of layered articles, samples were cut into 1.5×1.5 $cm^2$ coupons and contaminated on the colored external layer with 20 μL solution containing $2\times10^5$ *B.*

*anthracis* spores on each coupon. The coupons were cut from articles newly-treated by the method of Example 9, 2 months after treatment by the method of Example 9 or untreated (negative control). The coupons were left to dry for 24 h and were transferred into petri dishes containing Tryptose agar medium. The dishes were incubated in 37° C. for 10 days and bacterial growth was monitored.

No bacterial growth was evident on any treated coupon, regardless of the tested concentration. In sharp contrast, coupons from the untreated articles showed high bacterial growth.

This example illustrates that polymer compositions according to exemplary embodiments of the composition impart anti-bacterial properties to layered articles via spray treatment of the outer layer.

Example 11

Chlorine Desorption and Particle Emission from Safety of Treated Layered Articles In order to quantify chlorine desorption measurement of chlorine desorption (TLV=0.5 ppm) was carried out in two methods.

In the first method a treated article was placed in a testing system that applied through the article an air flow of 30 L/min, and continuous chlorine detection was performed at the inner side, at room temperature and 50% relative humidity.

In the second method chlorine desorption from the treated article was evaluated under harsher conditions. Samples of sprayed articles (8.9 $cm^2$) were inserted into a column placed in a continuous air flow system, at controlled temperature and relative humidity. The samples were tested at air flow of 1 L/min, temperature of 30° C. and relative humidity of 0% or 80%. Chlorine detection was carried out by an electrochemical detector (Dragger) with detection sensitivity of 0.01 ppm.

For the first method two articles treated with additives T-Cl and Ox-Cl respectively (10 mg per article), no chlorine was measured above 0.01 ppm for 40 minutes (TLV=0.5 ppm).

For the second method using the flow column system with relative humidity of 0% two articles treated with additives T-Cl and Ox-Cl respectively (10 mg per article) no chlorine was measured above 0.01 ppm for 50 minutes (TLV=0.5 ppm).

Figure 4:
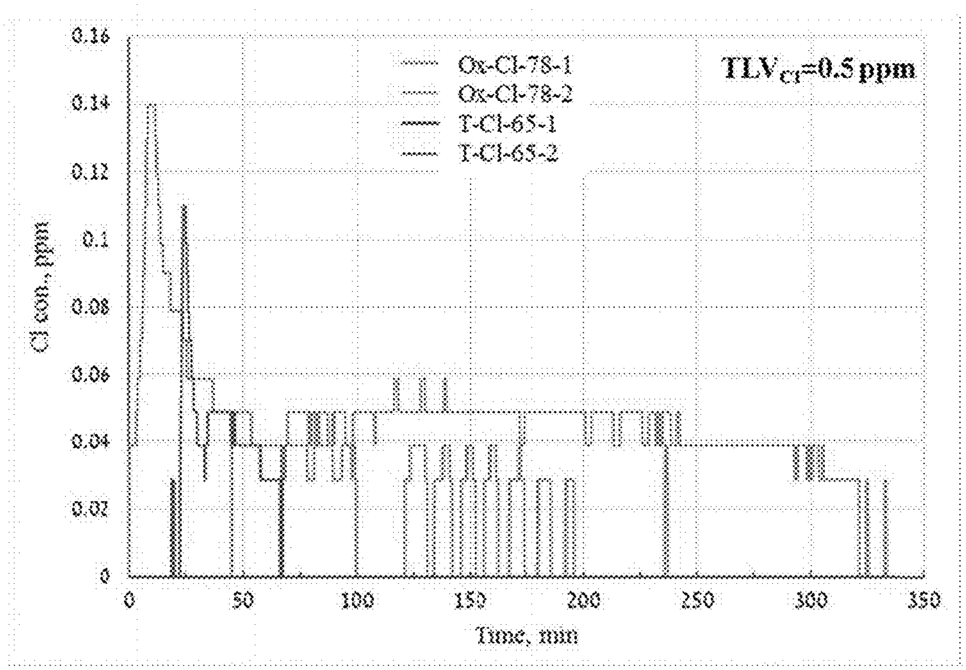
FIG. 4 is a histogram of detected chlorine levels in ppm as a function of test time in minutes for an exemplary embodiment of the invention.

For the second method using the flow column system with relative humidity of 75-80% for ~5.5 hours two articles treated with additives T-Cl (chlorinated trimelamine benzene tricarboxamide) and Ox-Cl (poly(tetrachloromelamine-co-oxalyl)) respectively (10 mg per article; two sample each) results are shown in FIG. 4.

FIG. 4 is a histogram showing detected chlorine levels as a function of test time.

Results presented in FIG. 4 show that the desorbed chlorine levels of articles treated by any additive, were lower than TLV throughout the ~5.5 hour test. One T-Cl-65 treated sample showed no chlorine desorption at all (red), in contrast to the other sample (green). This discrepancy between duplicate articles with the same treatment may be an artifact caused by variation of spray uniformity during application.

Particles emitted from treated articles were gravimetrically analyzed after collection on filter paper (>0.22 μm) at the exit of the column. Prior and post analysis, the filter paper was dried in an oven at 95° C. for 40 minutes and 40° C. for 1 hour, respectively, to reduce the effect of humidity absorbance.

No emitted particles were measured for an Ox-Cl treated article (10 mg per article) during 1 hour of air flow. A T-Cl treated article (10 mg per article) emitted 0.15 mg particles, as compared to the initial weight of filter paper.

This amount was emitted from a sample of 8.9 $cm^2$ area. If this is extrapolated to a larger area of 128 $cm^2$, 2 mg are expected to be emitted.

Due to these particle emission results, all subsequent experiments (e.g. animal tests) were carried out with Ox-Cl.

In summary, articles sprayed externally with chlorinated polymers according to exemplary embodiments of the invention showed less than TLV concentrations of chlorine desorption over 5.5 h at a humid environment, mimicking regular use. Particles were not shown to emit from Ox-Cl-78 treated articles and at a small amount from T-Cl-65 treated articles.

This example illustrates that chlorine desorption from an article treated with a chlorinated polymer according to an exemplary embodiment of the invention is negligible during a 4 to 12 hours use.

Example 12

In Vivo Experimental System Using a Rat Model

In order to evaluate the health impact of products according to the invention, treated layered articles developed and tested in Examples 7 through 11 were used, and a rat model system was established.

Chlorinated Polymer Treatment Material

As in previous examples, Ox-Cl-78, a chlorinated halamine polymer (Molecular Weight of 1 polymer unit=180 g/mole; Purity>95%; Batch number: DM-4212-78) was employed. It is referred to throughout this application as Ox-Cl DM 4212-78.

Animals:

Twenty-Four male rats (Sprague-Dawley; SD) weighing between 280 g to 305 g on the dosing day, were supplied by Envigo RMS Israel, LTD.

The animals were allowed to acclimatize for 3 days at the testing facility prior to study initiation.

Animals were housed 2-3 per cage (a single rat was individually housed), in a controlled environment with a temperature of 21±2° C. and a 12-h light/dark cycle with lights on at 6 am. Food and water were available ad libitum.

The experimental protocol was approved by the committee for animal care and use, designed to prevent or minimize any unnecessary pain and stress. Animals that lost more than 20% of their body weight (from pre-dose weight) were euthanized.

One day before administration of the test material, the animals were weighed and individually tagged by a tail mark. Animals were randomly allocated to the experimental groups. A respiratory function baseline was recorded by the whole-body plethysmography (Buxco, DSI, Harvard Bioscience Inc).

Only healthy animals were allowed to participate in this study.

Route of Administration:

The intranasal route of administration was selected in this study because it approximates the possible human exposure to Ox-Cl DM 4212-78 under clinical setting, when it will be applied on a fabric, e.g., bed sheets, pillow cases, coverlets, etc.

Dosing Formulation, Dosing Procedures and Dosing Volume:

Compound Ox-Cl-78 was first suspended in 100% acetone, and then diluted with saline to achieve a final formulation of 80% acetone/saline. These suspensions were freshly prepared on the dosing day.

A vehicle-control group (80% acetone/saline) was included in this study to evaluate possible adverse effects of acetone.

The dosing formulation was administered to both nostrils of anaesthetized rats (5% isoflurane/95% air) using a micropipette-tip inserted approximately 1-2 mm into the nostril. The total dosing volume (up to 50 μl, see Table 3) was subdivided into smaller drops of up to 13 al/nostril, in order to allow appropriate nasal absorption.

Study Design and Dose Level Justification:

The rats were dosed with Compound Ox-Cl-78 formulation, its vehicle or saline, as listed in Table 3.

TABLE 3

Dosing schedule by treatment group

| Group | Dose level (mg/kg) | # animals/ group (males) | Dose Concentration (mg/mL) | Dose Volume (for 280 g rat) |
|---|---|---|---|---|
| Saline | — | 2 | — | 50 μl |
| Vehicle | — | 2 | — | 50 μl |
| Low dose | 0.75 | 5 | 16.8 | 12.5 μl |
| Mid-Low dose | 3 | 5 | 16.8 | 50 μl |
| Mid-High dose | 10 | 4 | 56 | 50 μl |
| High dose | 30 | 6 | 168 | 50 μl |

Differences in relative nasal surface area between humans and rats (160 $cm^2$ in humans; 13.4 $cm^2$ in rats; see Erdo, F. et al. Brain Research Bulletin, 2018, 155-170), as well as differences in body surface area (using allometric scaling, $K_m$ ratio=6.2 for human to rat conversion, which relates to systemic effects) were considered. The equivalent human dose was calculated and is presented in Table 4.

TABLE 4

Correspondence between dosages in rats and dosages in humans

| Dose level, mg/kg (mg/rat; 280 g) | Equivalent human dose in mg, for a 60 Kg human Based on nasal surface area | Equivalent human dose in mg, for a 60 Kg human Based on body surface area |
|---|---|---|
| 0.75 (0.21) | 2.5 | 7.26 |
| 3 (0.84) | 10 | 29 |
| 10 (2.8) | 33 | 97 |
| 30 (8.4) | 100 | 290 |

Example 13

Clinical Observations and Sample Collections

Animals were observed for clinical signs on the dosing day (immediately after dosing and 1, 2 and 4-hours post dosing), and once daily during the recovery period (excluding the weekend). Careful consideration was given to any respiratory adverse effect (breathing distress, breathing sounds), and to skin irritations/lesions around the eyes and nose.

Changes in body weight were recorded once daily (excluding the weekend).

The effects of Ox-Cl on respiratory parameters (respiratory rate, tidal volume, enhanced pause, peak inspiratory and expiratory flow, ratio of achieving pick expiratory flow) were evaluated in the conscious rats, by whole body plethysmography. Measurements continued for 30 minutes, and were carried out at baseline (Day −1), 10-30 minutes after dosing, and during the recovery period at 24 hours, 3 days, and 6 days post dosing.

Necropsy:

At the end of the recovery period (or when an end-point parameter was met), the animals were euthanized. Blood samples were collected (by intracardial puncture) for hematology and chemistry analyses. Lungs, Trachea and nasal cavity were collected and preserved in 4% NBPF for possible future histological examination.

Mortality and Morbidity:

There were no premature deaths in the study. Five animals (4 from the 30 mg/kg dose group and 1 from the 10 mg/kg dose group) were euthanized 72 hours post-dosing as they have lost >20% of their body weight (compared to pre-dosing values), and showed severe respiratory clinical signs.

Figure 6:
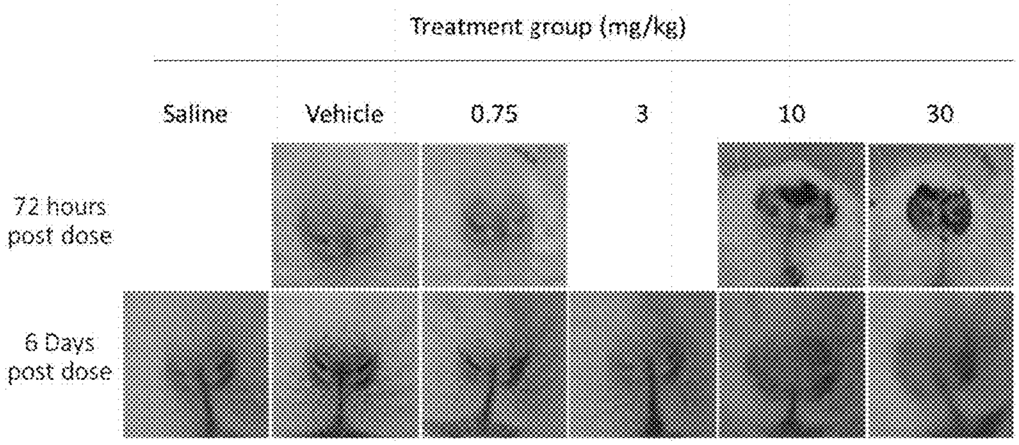
FIG. 6 is a series of photographs illustrating appearance of nostrils at 72 hours and 6 days post-dosing by treatment group for a toxicity evaluation experiment conducted on rats using an exemplary embodiment of the invention.

Body Weights:

Changes in body weight were monitored daily (excluding the weekend, FIG. 6).

Figure 5:
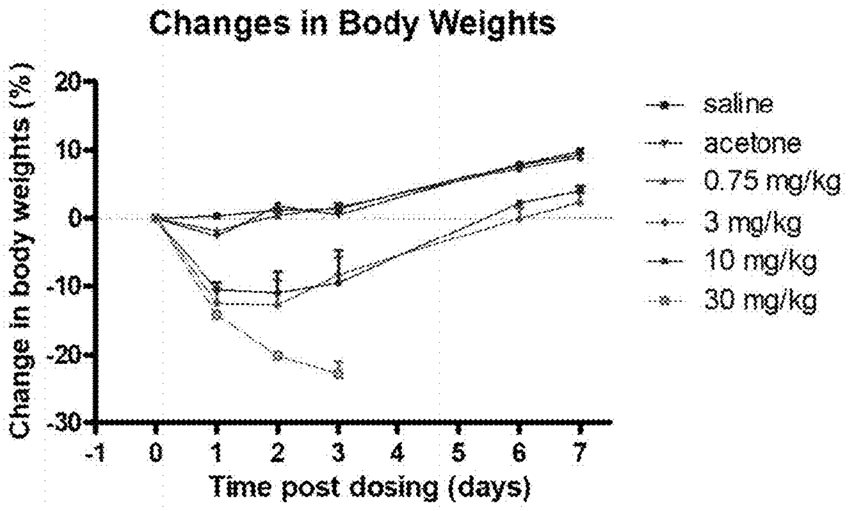
FIG. 5 is a histogram of percent change in body weight as a function of days post dosing for an experiment conducted on rats using an exemplary embodiment of the invention.

FIG. 5 is a histogram of change in body weight (%) as a function of time compared to pre-dosing values (Day 0) of treated and control group animals.

In animals from the 0.75 mg/kg group and in 3 (out of 4) control animals, a minor decrease in body weight (up to −3%) was observed 24 hours post-dosing. However, this decrease was attributed to the dosing day handling and procedures conducted on the day of dosing, and were not considered to be toxicologically meaningful. From 48 hours post-dosing and throughout the study period, body weight gain was observed for all these animals, and was comparable between the 0.75 mg/kg group animals and the control animals Body weight loss (compared to pre-dosing values) was observed in the 3, 10 and 30 mg/kg group animals at 24- and 48-hours post-dosing (−10 to −20%). At 72 hours post-dosing, most animals from the 3 and 10 mg/kg groups started to gain weight and reached pre-dosing values at the end of the study period.

In 4 (out of 6) animals from the 30 mg/kg group, and in a single animal from the 10 mg/kg group, body weight loss continued 72 hours post-dosing (up to −26%) and was correlated with a severe respiratory distress. These animals were therefore euthanized (in line with the end-point criterion). The remaining 2 animals in the 30 mg/kg group, which showed a body weight loss of −14 and −20% at 72 hours post-dosing, started to gain weight and reached a mean body weight in the range of pre-dosing values at Day 7 (−3%, data not shown).

Results presented in FIG. 5 indicate that doses up to 10 mg/kg were well tolerated from the standpoint of changes in body weight.

Example 14

Clinical Signs in the In Vivo Study

In order to examine the effect of the different treatment regimens in more detail, additional clinical data was gathered and analyzed.

Clinical evaluation was performed immediately following compound administration and at three different time points during that day.

No clinical signs were observed in the saline control group.

The 0.75 mg/kg and vehicle control group animals have shown no apparent breathing difficulties, however demonstrated imbalanced walk, swollen nose, half-closed eyes and nose irritation. These signs were resolved within an hour. No additional clinical signs were observed for 0.75 mg/kg and vehicle control group animals throughout the study period.

Administration of 3 mg/kg, 10 mg/kg and 30 mg/kg, led to a dose dependent presentation of respiratory clinical signs (breathing difficulties as manifested by open mouth breathing, head tilt and breathing sounds of choking), porphyrin staining around eyes and nostrils and swollen red nose. Reduced activity was also observed soon after dosing but resolved within the first 24 hours post-dosing.

Respiratory signs were resolved in the 3 mg/kg group by 72 hours post-dosing, however continued to manifest (at different severities) in the 10 and 30 mg/kg group animals.

At 72 hours post-dosing, all animals from the 30 mg/kg group, showed severe respiratory adverse effects which included difficulties of breathing and intense breathing sounds. 4 out of 6 of these animals (and also 1 animal from the 10 mg/kg group) reached the end-point of >20% body weight loss and were euthanized.

The 2 remaining animals from the 30 mg/kg group showed respiratory distress until the end of the study.

The respiratory clinical signs are consistent with the body weight change data presented above.

Nostril Skin Damage:

Swelling and irritation around the nostrils were observed immediately post-dosing in all treated groups (and the vehicle control group). This was in line with the observation that during dosing, some of the compound (and its vehicle) adhered to the outer surface of the nostrils.

Skin irritation was resolved within the first hour post-dosing in the 0.75 mg/kg and 3 mg/kg group and in the vehicle-control group animals.

FIG. 6 is a series of photographs illustrating appearance of nostrils at 72 hours and 6 days post-dosing by treatment group.

In the 10 and 30 mg/kg group animals, skin damage developed gradually, and a local and superficial burn around the nostrils was evident 72 hours post-dosing as seen in FIG. 6. This burn was resolved for most of the animals that reached the end of the study (7 Days post-dosing).

Example 15

Lung Function

In order to determine lung function, whole body plethysmography (WBP) was used. Baseline values of breathing were recorded a day before the test material was administered. On day of dosing (0) The WBP was performed immediately following dosing, up to 30 min from administration.

The following seven respiratory parameters were used to differentiate between groups.

Figure 7:
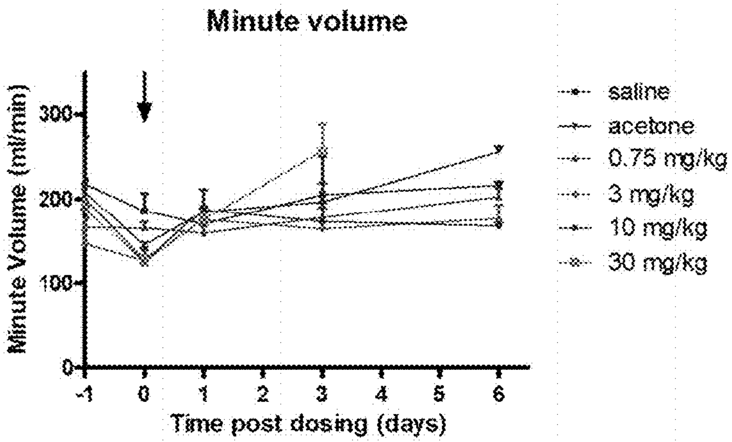
FIG. 7 is a histogram of minute volume as a function of time in days post treatment for a toxicity evaluation experiment conducted on rats using an exemplary embodiment of the invention.

(1) Minute volume (calculated rate of ventilation) was lower in the acetone, 3, 10 and 30 mg/kg group animals compared to saline group on dosing day (FIG. 7). No such difference was found for the 0.75 mg/kg group animals. No differences in the rate of ventilation were evident at 24 and 72 hours post-dosing. FIG. 7 is a histogram of minute volume as a function of time in days post treatment. The time course of minute volume (ml/min) following administration of compound 78 in whole body plethysmography (WBP) is expressed as mean±SEM for each treatment group. Measurements at day 0 were carried out immediately after dosing (marked by arrow).

Figure 8:
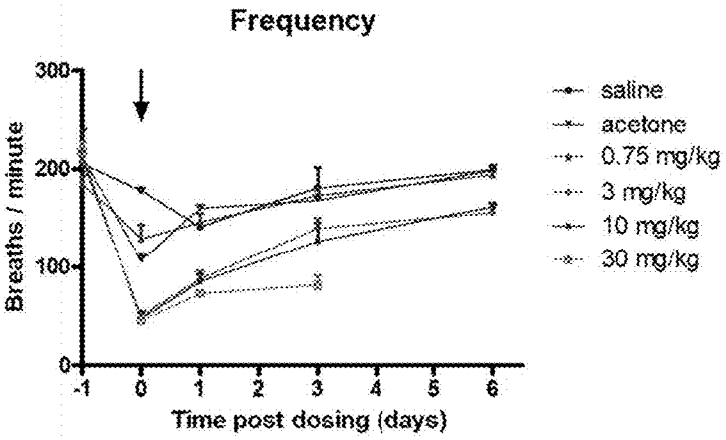
FIG. 8 is a histogram of breathing frequency (breaths/min) as a function of time in days post treatment for a toxicity evaluation experiment conducted on rats using an exemplary embodiment of the invention.
Figure 10:
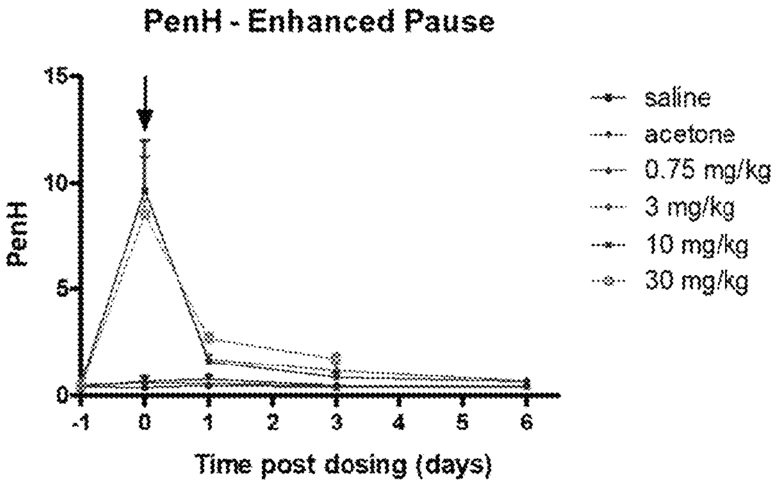
FIG. 10 is a histogram of Enhance Pause (PenH) as a function of time in days post treatment for a toxicity evaluation experiment conducted on rats using an exemplary embodiment of the invention.

(2) The frequency of breathing was influenced by administration of 3, 10 and 30 mg/kg doses (FIG. 10). In these groups, immediately following administration, lower rates of breathing (BPM) were measured in comparison to the 0.75 mg/kg, vehicle or saline group animals. This effect lasted throughout the entire period of the experiment. The 0.75 mg/kg group animals' frequency of breathing was similar to that of the vehicle control group. FIG. 8 is a histogram of breathing frequency (breaths/min) as a function of time in days post treatment. The time course of breathing frequency (breaths/min) following administration of compound 78 in whole body plethysmography (WBP) is expressed as mean±SEM. Measurements at day 0 were carried out immediately after dosing (marked by arrow).

Figure 9:
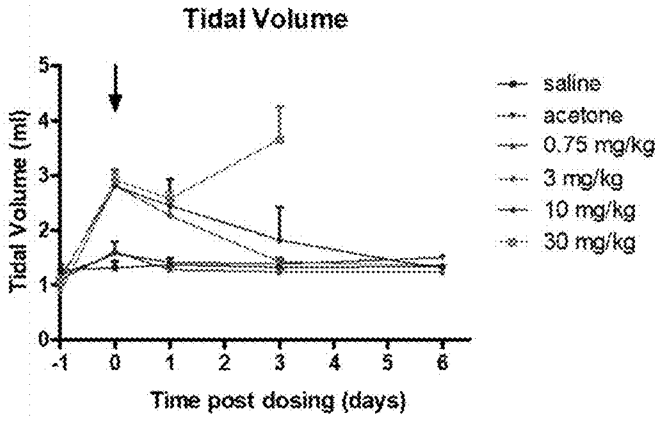
FIG. 9 is a histogram of Tidal Volume as a function of time in days post treatment for a toxicity evaluation experiment conducted on rats using an exemplary embodiment of the invention.
Figure 11:
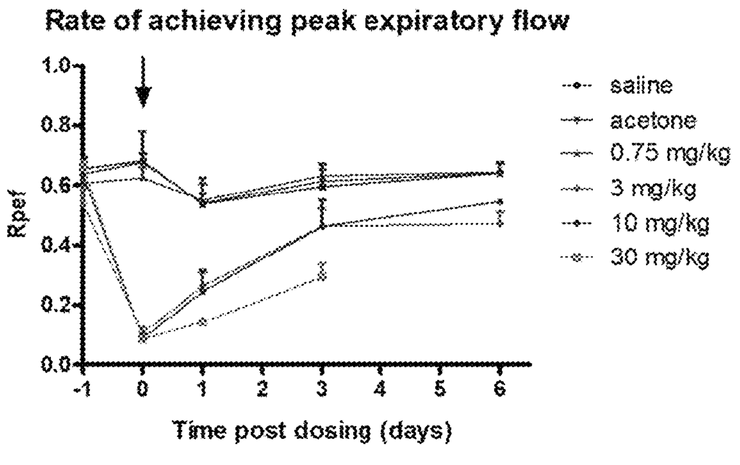
FIG. 11 is a histogram of rate of achieving peak expiratory flow (Rpef) as a function of time in days post treatment for a toxicity evaluation experiment conducted on rats using an exemplary embodiment of the invention.

(3) An increase in Tidal volume (volume inhaled) was found in the 3, 10 and 30 mg/kg groups following administration on dosing day and 24 hours post-dosing (FIG. 11). The effect was transient for the 3 and 10 mg/kg groups and completely vanished by the end of the study period. No changes in tidal volume were found for the 0.75 mg/kg group animals throughout the study period. FIG. 9 is a histogram of Tidal volume (volume inhaled) as a function of time in days post treatment. The time course of tidal volume (ml) following administration of compound 78 in whole body plethysmography (WBP) is expressed as mean±SEM. Measurements at day 0 were carried out immediately after dosing (marked by arrow).

(4) A major increase in enhanced pause (PenH), an indicator of bronchoconstriction, was found in the 3, 10 and 30 mg/kg groups immediately after administration (FIG. 10). This effect, though smaller, was also evident 24 hours and 6 days post administration. No increase in enhanced pause was found in the 0.75 mg/kg group (similar values to control groups). FIG. 10 is a histogram of enhanced pause (PenH) as a function of time in days post treatment. The time course of enhanced pause (PenH) following administration of compound 78 in whole body plethysmography (WBP) is expressed as mean±SEM. Measurements at day 0 were carried out immediately after dosing (marked by arrow).

(5) The rate of achieving peak expiratory flow (Rpef) was lower in the 3, 10 and 30 mg/kg groups (FIG. 11). The decreased rate in these groups was reduced throughout the study period, though did not vanish before the end of the study period.

FIG. 11 is a histogram of rate of achieving peak expiratory flow (Rpef) as a function of time in days post treatment. The time course of rate of achieving peak expiratory flow (Rpef) following administration of compound 78 in whole body plethysmography (WBP) is expressed as mean±SEM. Measurements at day 0 were carried out immediately after dosing (marked in arrow).

Figure 12A:
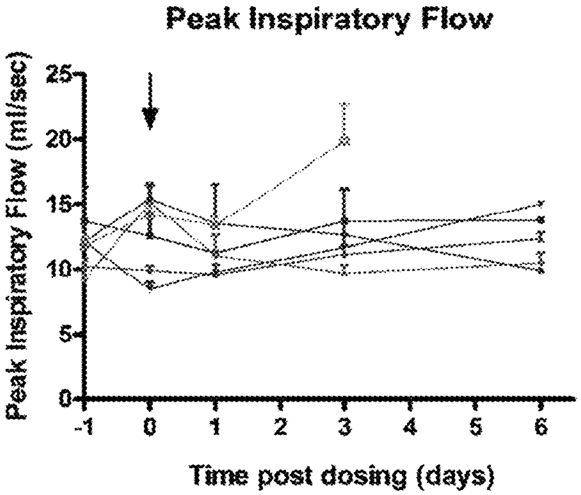
FIG. 12A is a histogram of peak inspiratory flow (PIF) as a function of time in days post treatment for a toxicity evaluation experiment conducted on rats using an exemplary embodiment of the invention.
Figure 12B:
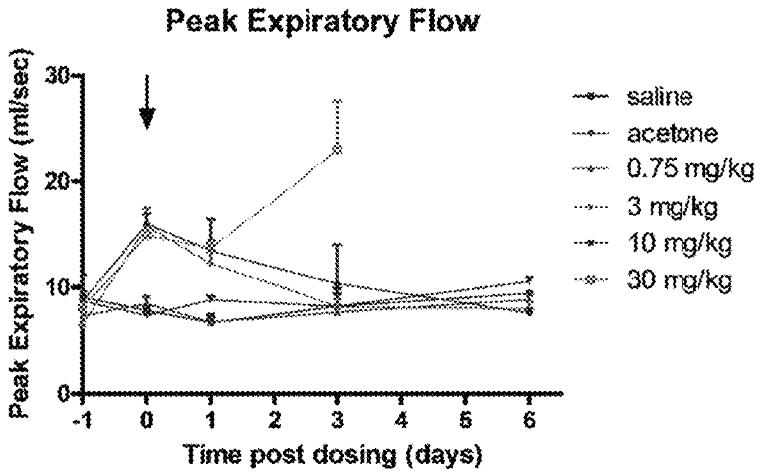
FIG. 12B is a histogram of peak expiratory flow (PEF) as a function of time in days post treatment for a toxicity evaluation experiment conducted on rats using an exemplary embodiment of the invention.

(6) The peak inspiratory flow (PIF) in the 3, 10 and 30 mg/kg groups was higher than in the control group when measured on the dosing day (FIG. 12A). This effect was not evident in the 0.75 mg/kg group animals. Interestingly, on day 6 the PIF of the 3, 10 and 30 mg/kg groups was lower than control animals. Similar results are shown for the values of peak expiratory flow (PEF; FIG. 12B): higher peak flow immediately after administration, and lower peak flow on day 6. FIG. 12A is a histogram of peak inspiratory flow (PIF) as a function of time in days post treatment. FIG. 12B is a histogram of peak expiratory flow (PEF) as a function of time in days post treatment. The key is common to both panels of the figure. The time course of peak inspiratory flow (PIF) (FIG. 12A) and peak expiratory flow (PEF) (FIG. 12B) following administration of compound 78 in whole body plethysmography (WBP) is expressed as mean±SEM. Measurements at day 0 were carried out immediately after dosing (marked by arrow).

(7) The time spent inhaling (FIG. 13A) and exhaling (FIG. 13B) during each breath was higher on the dosing day following administration and throughout the study period, for the 3, 10 and 30 mg/kg group animals, compared to 0.75 mg/kg and acetone groups which presented only a short transient increase.

Figure 13A:
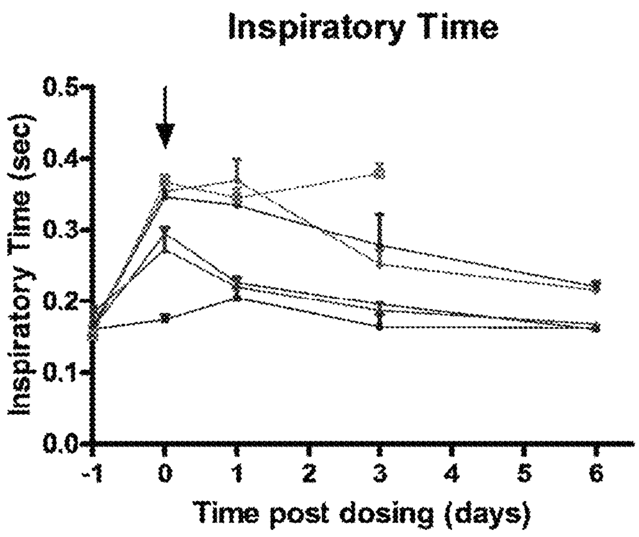
FIG. 13A is a histogram of time spent inhaling as a function of time in days posttreatment for a toxicity evaluation experiment conducted on rats using an exemplary embodiment of the invention.

FIG. 13A is a histogram of time spent inhaling as a function of time in days post treatment.

Figure 13B:
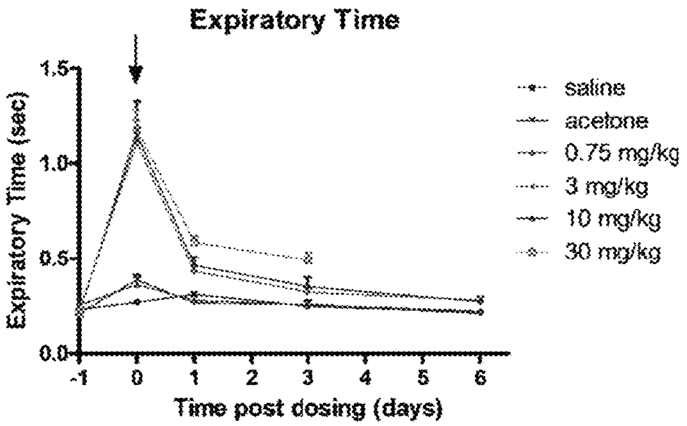
FIG. 13B is a histogram of time spent exhaling as a function of time in days post treatment for a toxicity evaluation experiment conducted on rats using an exemplary embodiment of the invention.

FIG. 13B is a histogram time spent exhaling as a function of time in days post treatment. The key is common to both panels of the figure. The time course of time spent inhaling (FIG. 13A) and exhaling (FIG. 13A) following administration of compound 78 in whole body plethysmography (WBP) is expressed as mean±SEM. Measurements at day 0 were carried out immediately after dosing (marked by arrow).

Example 16

Hematology and Blood Chemistry Evaluation

Blood hematology and chemistry analyses were completed for the early-euthanized animals at 72 hours post-dosing, and for the rest of the animals at the end of the study period (Day 7). For the purpose of the statistical analysis, the saline and vehicle control group animals (n=2 per group), which showed a similar measured value, were considered as a single control group.

Overall, for the 30 mg/kg group animals and for the early-euthanized animals, the hematology and chemistry profile indicated dehydration, and included a decrease in alkaline phosphatase (ALP), amylase, glucose and blood urea nitrogen (BUN) but with no changes in creatinine levels (compared with control animals). A mild decrease in phosphate and calcium levels were also observed in these animals. In addition, in these animals, higher hematocrit, RBC count and hemoglobin (polycythemia) were presumably an additional indicative of dehydration and low food intake (in agreement with the observed fall in body weights).

Statistically significant increase in alanine aminotransferase (ALT) values was observed in 30 mg/kg group animals and in the early-euthanized animals, compared with control animals (~70 vs ~50 U/L, respectively).

A mild, but statistically significant decrease in mean WBC counts was observed in animals from the 0.75-10- and 30 mg/kg groups compared with controls. In addition, statistically significant decrease in lymphocyte and neutrophil counts (compared with controls) was observed in some of the treated groups. Nevertheless, no significant changes in % lymphocytes and % neutrophils were observed in the 0.75, 3 or 10 mg/kg group animals. In addition, no changes were observed in platelet levels in all the treated groups. Lastly, the decrease in WBC count was not dose-dependent. Therefore, the biological relevance of the changes in WBC counts could not be assessed.

Results from all the analyses associated with the in-vivo study (Examples 12-16) indicate that the No Adverse Effect Level (NOAEL) of compound Ox-Cl-78, based on respiratory function and clinical pathology, appears to be 0.75 mg/kg, when administered intranasally to rats. It should be noted, that histological evaluation of the nasal cavity and lungs was not performed and therefore was not taken into consideration when determining the NOAEL.

These results suggest a Draize irritation test on rabbit skin should be performed.

Example 17

Draize Irritation Test on Rabbit Skin

In order to determine the effect of a polymer according to the invention on skin under actual use conditions polypropylene non-woven fabric SMS were sprayed with an acetone solution of poly(tetrachloromelamine-co-oxalyl). Each article (210 $cm^2$) was treated with 5 mg of polymer.

For the Draize test, 8 cm×8 cm pieces of treated and untreated fabric were cut and applied on the shaved backs of rabbits (male and female). The pieces were fixed on the rabbits backs for 24 h, followed by a weeklong observation and scoring. The treated fabric squares did not cause any irritation to rabbit skin, and appear to be safe.

The invention claimed is:

1. A polymer comprising:

(a) a plurality of melamine monomers; and (b) at least one oxalyl linker between each pair of said monomers, wherein said monomers and linkers are connected linearly or in a branched chain.

2. The polymer according to claim 1, wherein said monomers and linkers are connected in a net like fashion.

3. The polymer according to claim 2, wherein at least some of the melamine of said monomers are connected to at least 2 of said oxalyl linkers.

4. The polymer according to claim 3, wherein at least some of the melamine of said monomers are connected to 3 of said oxalyl linkers.

5. A composition comprising:

the polymer according to claim 1 and a solvent in which said polymer is dissolved.

6. The composition according to claim 5, incorporated into a paint, ink or dye.

7. The composition according to claim 5, provided in a spray bottle.

8. A fabric treated with the composition according to claim 5.

9. An article of manufacture comprising the polymer as claimed in claim 1.

* * * * *